United States Patent [19]
Gattone, II

[11] Patent Number: 5,972,882
[45] Date of Patent: Oct. 26, 1999

[54] TREATMENT OF POLYCYSTIC KIDNEY DISEASE USING VASOPRESSIN $V_2$ RECEPTOR ANTAGONISTS

[75] Inventor: Vincent H. Gattone, II, Overland Park, Kans.

[73] Assignee: University of Kansas Medical Center, Kansas City, Kans.

[21] Appl. No.: 09/211,396

[22] Filed: Dec. 14, 1998

Related U.S. Application Data

[60] Provisional application No. 60/069,487, Dec. 15, 1997.

[51] Int. Cl.$^6$ ..................................................... A61K 38/00
[52] U.S. Cl. .............................................................. 514/11
[58] Field of Search ........................................... 514/2, 11

[56] References Cited

U.S. PATENT DOCUMENTS

| | | | |
|---|---|---|---|
| 4,749,782 | 6/1988 | Huffman et al. | 530/328 |
| 4,826,813 | 5/1989 | Huffman et al. | 514/11 |
| 4,876,243 | 10/1989 | Marshall et al. | 514/11 |

OTHER PUBLICATIONS

Martinez–Maldonado et al., "Adult Polycystic Kidney Disease: Studies of the Defect in Urine Concentration", *Kidney International*, 2:107–113 (1972).

Danielsen et al., "Exaggerated Natriuresis in Adult Polycystic Kidney Disease", *Acta Med Scand*, 219:59–66 (1986).

Danielsen et al., "Expansion of Extracellular Volume in Early Polycystic Kidney Disease", *Acta Med Scand*, 219:399–405 (1986).

Mangoo–Karim et al., "Renal Epithelial Cyst Formation and Enlargement In Vitro: Dependence on cAMP", *Proc. Natl. Acad. Sci. USA*, 86:6007–6011 (1989).

Gabow et al., "The Clinical Utility of Renal Concentrating capacity in Polycystic Kidney Disease", *Kidney International*, 35:675–680 (1989).

Grant et al., "Arginine Vasopressin Stimulates Net Fluid Secretion in a Polarized Subculture of Cyst–Forming MDCK Cells", *Journal of the American Society of Nephrology*, 2:219–227 (1991).

Yamaji et al., "Localization of Two Types of Aquaporin in Autosomal Dominant Polycystic Kidney Disease (ADPKD) Cells", *Journal of the American Society of Nephrology*, 6:729 (1995).

Devuyst et al., "Expression of Aquaporins–1 and –2 During Nephrogenesis and in Autosomal Dominant Polycystic Kidney Disease", *The American Physiological Society*, 271:F169–F183 (1996).

Welling et al., "Cystic and Developmental Diseases of the Kidney", *Brenner & Rector's —The Kidney (Fifth Edition)*, vol. II:1828–1863 (1996).

Aziz et al., "Aberrant 11β–Hydroxysteroid Dehydrogenase–1 Activity in the cpk Mouse: Implications for Regulation by the Ke 6 Gene", *Endocrinology*, 137(12):5581–5588 (1996).

Hayashi et al., "Expression and Localization of the Water Channels in Human Autosomal Dominant Polycystic Kidney Disease", *Nephron*, 75(3):321–326 (1997).

Mark A. Knepper, "Molecular Physiology of Urinary Concentrating Mechanism: Regulation of Aquaporin Water Channels by Vasopressin", *American Journal of Physiology*, 272:F3–F12 (1997).

Yamaguchi et al., "Renal Accumulation and Excretion of Cyclic Adenosine Monophosphate in a Murine Model of Slowly Progressive Polycystic Kidney Disease," *American Journal of Kidney Disease*, 30(5):703–709 (1997).

Gattone II, et al., "Collecting Duct Gene Expression and Effect of an AVP–V2 Receptor Antagonist on the Progression of PKD in PCY Mice", *Journal of American Society of Nephrology*, 9:19A (1998).

Gattone II, et al., "In Vitro and In Vivo Modulation of Collecting Duct mRNA Expression in Infantile Polycystic Kidney Disease (PKD) in CPK Mice", *Journal of American Society of Nephrology*, 9:19A (1998).

Gattone II, et al., "Developmental Expression of Urine Concentration–Associated Genes and Their Altered Expression in Murine Infantile–Type Polycystic Kidney Disease", *Developmental Genetics*, 24:1–10 (1999).

*Primary Examiner*—Raymond Henley, III
*Attorney, Agent, or Firm*—Sonnenschein Nath & Rosenthal; Joseph A. Mahoney; Arjun S. Sanga

[57] ABSTRACT

The present invention is directed to the novel treatment of ARPKD and ADPKD by administering a pharmacologically effective amount of a $V_2$ receptor antagonist. Orally active $V_2$ receptor antagonists such as OPC-31260, OPC-41061, SR121463A and VPA-985 are administered alone, or in combination to mammalian PKD subjects to reduce the cAMP generated by the increased expression of AVP-$V_2$ receptor, AQP2 and AQP3, thereby reducing and/or preventing cyst enlargement.

9 Claims, 16 Drawing Sheets

AVP-V2 Receptor

Aquaporin 2

Aquaporin 3

N C   N C   N C   N C   N N C C
7 day  10 day  14 day  17 day    21 day

Methylene Blue

18S rRNA

AVP-V2 Receptor

Aquaporin 2

Aquaporin 3

Ctrl EGF   Ctrl EGF   Ctrl EGF   Ctrl EGF
 Normal     Cystic     Normal     Cystic
  2 weeks              3 weeks

TREATMENT OF POLYCYSTIC KIDNEY DISEASE USING VASOPRESSIN $V_2$ RECEPTOR ANTAGONISTS

RELATED APPLICATION

This application is based on Provisional Application Ser. No. 60/069,487 filed Dec. 15, 1997.

FIELD OF THE INVENTION

This invention relates to the treatment of polycystic kidney disease and, more particularly, to the use of vasopressin $V_2$ receptor antagonists to reduce the cAMP generated by the increased expression of vasopressin $V_2$ receptor, aquaporin-2 and aquaporin-3 after stimulation by arginine vasopressin.

BACKGROUND OF THE INVENTION

Polycystic kidney disease (PKD) is the most common inherited cause of end-stage renal disease afflicting an estimated 1 in 500 to 1 in 1000 persons. The two most prominent, inherited forms of PKD are autosomal dominant (ADPKD) generally characterized as being asymptomatic until adulthood, while autosomal recessive (ARPKD) is usually symptomatic in the perinatal or infantile period. The genes for ADPKD (i.e., ADPKD1 or polycystin, and ADPKD2) have been cloned and sequenced. The functional role of these unique and very different proteins in initiating cysts is not known. The chromosomal locations for the ARPKD gene in humans and the mouse model (the C57BL/6J-cpk/cpk mouse) have been identified but neither gene has been cloned.

Renal cysts are among the most common pathological structures observed in kidneys. Mangoo-Karim et al., *Proc. Natl. Acad. Sci. USA,* 86: 6007–11 (1989).[1] Cysts derive from nephron and collecting duct tissue and are isolated collections of urine-like fluid surrounded by a continuous epithelial layer. Cysts may be solitary and relatively innocent or so numerous (i.e., polycystic) that they compress and distort normal parenchyma and thereby cause renal insufficiency. Mangoo-Karim et al., supra.

[1] All literature referred to herein is hereby incorporated by reference.

Renal cyst formation and enlargement is the product of a highly coordinated integration among three central processes: epithelial proliferation, fluid accumulation within the cyst cavity, and remodeling of the interstitium (matrix) that surrounds the cysts. Mangoo-Karim et al., supra. See also Cowley et al., *Proc. Natl. Acad. Sci. USA,* 84: 8394–98 (1987); Grantham et al., *Kidney Int.,* 31: 1145–52 (1987); Carone et al., *Am. J. Pathol.,* 130: 466–71 (1988); and Grantham et al., *Kidney Int.,* 35: 1379–89 (1989).

The development of PKD has two distinct phases—the initiation of cysts and cyst progression. The collecting duct is the major tubule affected by the cystic change in ARPKD, and is largely responsible for concentrating urine. Although the defective genes probably control the initiation of cysts, there are a number of factors which appear to contribute to the progression of PKD. Polyuria with a renal concentrating defect is found in virtually all forms of inherited PKD and may contribute to the progression of the cystic disease. The basis for this defect is not understood.

Urine concentration in the collecting ducts requires three conditions: (1) A hypertonic interstitium to serve as the osmotic gradient for directional water movement; (2) arginine vasopressin (AVP) and its collecting duct cell receptor (the AVP–$V_2$ receptor); and (3) stimulation of the water channels aquaporin-2 (AQP2) and aquaporin-3 (AQP3) by AVP such that AQP2 is inserted into the apical membrane while AQP3 is localized to the basolateral membrane. PKD produces a condition which appears similar in many respects to nephrogenic diabetes insipidus (DI). Inherited nephrogenic DI is usually caused by a defect in either the AVP–$V_2$ receptor or AQP2 genes, neither of which are affected by the ADPKD mutations. While preliminary data from Yamaji et al. (1995) indicate that ADPKD kidneys have AQP2, AVP stimulation of ADPKD cysts does not stimulate AQP2 insertion into the apical membrane. These data indicate an interesting and unique functional deficit in PKD. It is unclear why or when this collecting duct abnormality develops.

Gabow et al. (1989) described the concentrating defect as an early event which can be used for the identification of affected individuals within an ADPKD family. A number of researchers have looked at structural distortion, AVP, urinary concentrating ability, renal insufficiency and the renin-angiotensin system in hypertensive and normotensive ADPKD patients to determine relationships critical to the development of hypertension and progression to renal failure. The renal concentrating defect correlates positively with renal insufficiency and structural distortion of the kidney (Gabow et al., 1989). A role for atrial natriuretic peptide (ANP) (Sorenson et al., 1990), medullary architecture (Anand et al., 1975; Gabow et al., 1989), and an increase in aquaporin-1 (CHIP-28) (Bachinsky et al., 1995) are hypothesized to play a role. However, the basis for the concentrating defect remains elusive. Early studies described the renal concentrating defect as unresponsive to AVP (Martinez-Maldonado et al., 1972). It has been reported that AVP levels are elevated in hypertensive individuals with ADPKD (Danielson et al., 1986a), and all ADPKD patients after volume expansion with hypertonic saline, as compared to control (Danielson et al., 1986b). Therefore, the ligand appears to be present in elevated concentrations in those with ADPKD.

Data indicate that AVP binding to a small fraction of the receptors is sufficient to initiate a maximal response (Abramow et al., 1987) suggesting that ligand is generally the limiting factor. However, cultured ADPKD cells exhibited an attenuated response to AVP (Wilson et al., 1986) suggesting an inherent defect in the vasopressin receptor system as well.

This could be due to the abnormal response of cystic epithelial cells to AVP as described by Yamaji et al. (1995). Prior to Applicant's research described below, there was no literature on the expression AVP receptors in PKD.

Evidence from in vitro studies suggests that increased proliferation of epithelial cells and secretion of fluid by these cells may be important factors in the progressive enlargement of renal cysts. The rate of enlargement in vitro can be accelerated by cyclic adenosine 3'5' monophosphate (cAMP) and agonists that lead to the production of cAMP. See Mangoo-Karim et al., supra.

Research has been conducted examining the role of the cystic fibrosis transmembrane conductance regulator (CFTR) and the lipid cyst activating factor (CAF) in PKD. See, e.g., Davidow et al., *Kidney Int.* 50(1): 208–218 (1996); Yamaguchi et al., *Am. J. Kidney Dis.,* 30(5): 703–709 (November 1997). Both CFTR and CAF are mediated by cAMP, and thus far CAF has been implicated in increasing renal cAMP. Yamaguchi et al., supra. Activation of the vasopressin $V_2$ receptor is also mediated by G-proteins (guanyl nucleotide regulatory proteins) and cAMP. Carmichael et al., *Sem. in Nephrology,* 14(4): 341–48 (1994). However, more than 240 G-protein-coupled receptors have been cloned and those mediated by cAMP are abundant not only in the kidney but throughout the body. For example, cAMP may be abnormally increased by parathyroid hormone or prostaglandins. Thus, identifying the source(s) of increased cAMP and treating this imbalance has proved to be problematic.

Currently, there is no treatment for PKD other than agents to manage the sequelae of the disease. For example, angiotensin II inhibitors like captopril are often used to control the associated hypertension which is allegedly partially mediated by renin. Therefore, a definite need exists for therapies directed at the progression mechanisms of the disease.

SUMMARY OF THE INVENTION

It is, therefore, a principal object of this invention to provide a therapy to control the progression mechanisms of PKD. The present invention is directed to the novel treatment of ARPKD and ADPKD utilizing $V_2$ receptor antagonists, and particularly, orally bioavailable $V_2$ receptor antagonists. Orally active $V_2$ receptor antagonists such as OPC-31260, OPC-41061, SR121463A and VPA-985 are administered to mammalian PKD subjects to reduce the cAMP generated by the increased expression of AVP–$V_2$ receptor, AQP2 and AQP3, thereby reducing and/or preventing cyst enlargement. These and other objects and advantages of the present invention will be apparent from the attached drawings and description of the preferred embodiments.

DETAILED DESCRIPTION OF THE PREFERRED EMBODIMENT

Figure 1:
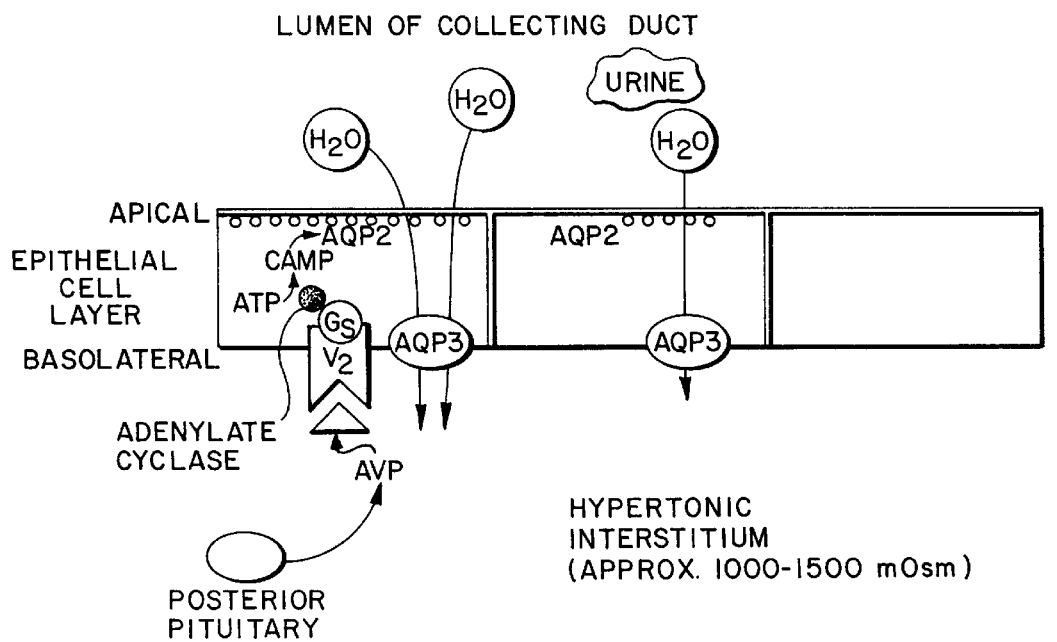
FIG. 1 is a cross-sectional illustration of the epithelial lining of the collecting duct of a normal mammalian kidney showing second messenger pathways for the vasopressin $V_2$ receptor intracellular signal transduction.

A ubiquitous problem associated with both inherited forms of PKD is a renal concentrating defect in that generally subjects having the disease can neither concentrate nor dilute their urine. Thus, PKD patients may be generally in a slightly dehydrated state. While this concentrating defect is not life threatening so long as adequate hydration is maintained, Applicant postulated and then found that it is the concentrating defect which induces a cascade of events which accelerates the progression of PKD. In the epithelial layer of a normal collecting duct, illustrated schematically in FIG. 1, AVP reacts with the vasopressin $V_2$ receptor which mediates AVP's anti-diuretic effect. AVP is released from the posterior pituitary gland upon sensation by the hypothalamus of an increase in blood osmolarity and/or decreased vascular volume. As mentioned previously, the $V_2$ receptor is coupled to a G-protein which regulates adenylate cyclase activity and the formation of cAMP. Amplification of the primary signal occurs with the activation of many G-proteins (of the same class) by a single ligand-bound receptor and the induction of several enzymatic cycles by each activated G-protein. See Carmichael et al., supra. AQP2 is the predominant AVP-regulated water channel of the kidney and is essential for regulation of body water balance. Fushimi, Sasaki, et al., *Nature* 361: 549–52 (1993). The cAMP generated by the AVP–$V_2$ receptor reaction causes AQP2 to be inserted into the apical plasma membrane. AQP3 is constitutively present in the basolateral plasma membrane of the collecting duct (CD) cells and has been found to also be increased by cAMP. The AQP2 and AQP3 water channels allow water to move from the urinary space into the hypertonic interstitium (about 1000–1500 mOsm), thereby concentrating the urine.

A. Altered Expression of Genes Associates with Renal Concentration in PKD

1. Background

Figure 2:
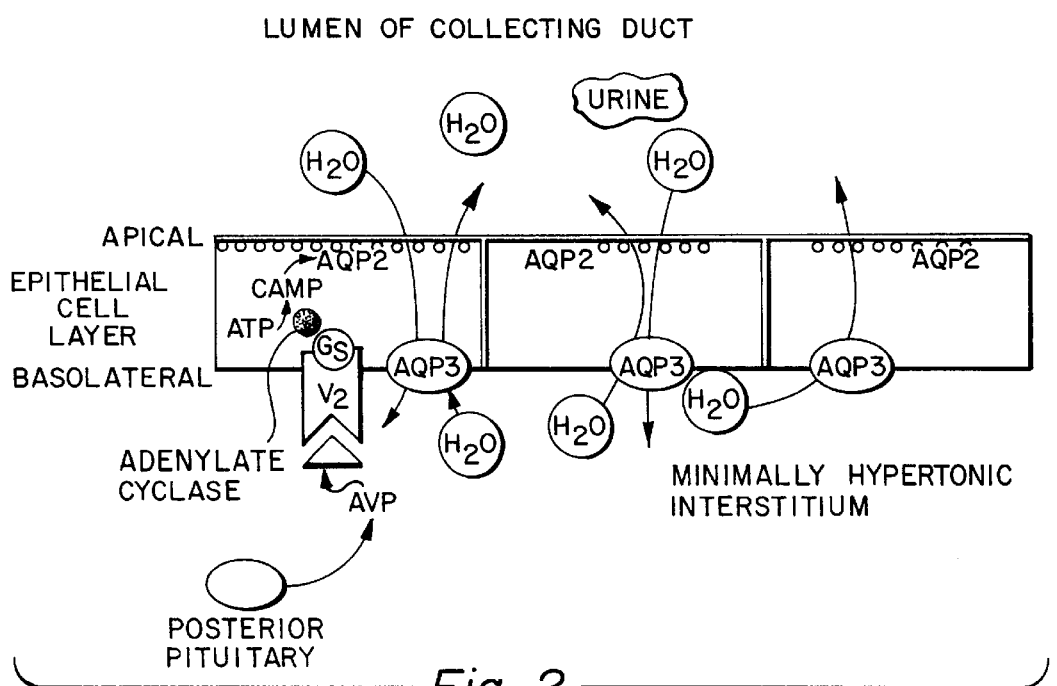
FIG. 2 is a cross-sectional illustration of the epithelial lining of the collecting duct of a mammalian kidney afflicted with PKD.

In the PKD kidney (FIG. 2), the medullary concentration gradient necessary for water reabsorption is not established and the interstitium is minimally hypertonic. Such patients cannot, therefore, properly concentrate urine. While there is a small body of literature on the development of urine concentrating capability, there are still many unanswered questions. See Spitzer & Schwartz (1992) for a review. Structurally, the abundance of medullary interstitium and the paucity of medullary vasculature in developing kidney may limit the ability of the kidney to establish a hypertonic medullary environment. Functionally, the collecting duct (CD) cells from the immature kidney do not respond to AVP (i.e., cAMP generation) as much as adult cells. The basis for this hyporesponsiveness is thought to be the low number of AVP–$V_2$ receptors in the immature kidney. Rajerison et al. (1976). Ervin et al. (1992) found that urinary osmolarity and volume is regulated by the AVP–$V_2$ receptor even in fetal sheep kidney. At present, it is unclear what regulates the expression or activity of the AVP–$V_2$ receptor. There is some evidence that exposure to AVP down-regulates the number of AVP receptors in adults. See Steiner & Phillips (1988). However, acute neonatal exposure to increased AVP on days 1 through 7 chronically up-regulated the number of liver AVP receptors. Szot et al. (1992). A number of factors may regulate the expression of AVP receptors. Epidermal growth factor (EGF), prostaglandin-$E_2$ ($PGE_2$) and atrial natriuretic peptide (ANP) can inhibit the functional activity of the AVP–$V_2$ receptor of CD cells. Applicant has found that EGF down-regulates AVP–$V_2$ receptor mRNA expression in normal CD cells in culture. This may be important since EGF is almost absent in the cystic kidneys of cpk mice. Horikoshi et al. (1991); Gattone et al. (1990). Therefore, its role in the down-regulation of AVP–$V_2$ receptor would be absent in the cpk kidney. In cpk cystic kidney, Applicant has found extremely high levels of AVP–$V_2$ receptor mRNA expression (explained below), possibly secondary to these low EGF levels. There is no data at present to even postulate a role for $PGE_2$ or ANP in the developmental concentration defect in neonates or PKD. ANP is normally expressed by fetal and neonatal medullary CD. McKenzie et al. (1991). Activation of the AVP–$V_2$ receptor stimulates adenylate cyclase activity and increases cAMP levels which cause the insertion of the AQP2 water channels in the apical cell membranes. Therefore, this water channel protein should not limit water movement unless it is not inserted into the collecting apical membrane. In PKD, a problem appears to be the inability of the AQP2 protein to insert into the membrane as described by Yamaji et al. (1995) for ADPKD cystic epithelial cells.

As stated above, the adenylate cyclase system has been implicated in the progression of cyst enlargement in vitro. Mangoo-Karim et al. (1989). Therefore, over stimulation of the AVP–$V_2$ receptor would lead to elevated levels of cAMP which could accelerate the enlargement of renal cysts. There is, however, no literature on the developmental expression/misregulation of genes associated with urinary concentration in kidneys developing PKD.

Applicant's research accordingly focused on the renal gene expression of AVP–$V_2$ receptor, AQP2, AQP3 and aldose reductase (AR) in different phases of PKD development in two murine models of PKD: C57BL/6J-cpk/cpk model (cpk) of infantile-type PKD and CD1-pcy/pcy model (pcy) of adult-type PKD.

2. Cpk Model

The cpk mouse (Gattone et al. 1988) develops a form of PKD which closely mimics the renal changes seen in human ARPKD. The cpk mice normally die of uremia by 4 weeks of age. Applicant has helped characterize the immature phenotype of the collecting duct cyst epithelium in the cpk mouse. Harding et al. (1991). Applicant has also characterized a role for the misexpression of EGF in the disease process. Gattone et al. (1990, 1995). This EGF abnormality may also contribute to the urine concentration defect.

The developmental expression of $V_2$ receptor, AQP2, AQP3 and AR mRNA was determined in 7, 10, 14, 17 and 21 day-old cpk cystic and phenotypic normal littermates. RNA was isolated from the kidneys of 0, 7, 14 and 21 day cpk and normal littermate mice. Total RNA from kidney was extracted by acid quanidium thiocyanate, phenol, chloroform method using TriReagent (Molecular Probes, Cincinnati, Ohio). Five (5) ug of total RNA was loaded per lane and electrophoresed in a formaldehyde, one percent (1%) agarose gel. The RNA was transferred to Zetabind. Blots were then stained with methylene blue to assure that the lanes were loaded equally, that the RNA was not degraded and that the RNA transferred appropriately. A photograph of the stained blot was recorded and analyzed for the equality of loading of each lane. The blot was then baked for 2 hours at 85° C.

Applicant obtained nucleic acid probes for the AVP $V_2$ receptor from Dr. Brownstein at NIMH, rat aquaporin 2 from Dr. A. S. Verkman at the University of California, San Francisco, mouse aquaporin 3 isolated by RT-PCR from rat kidney RNA in Applicant's laboratory, and human aldose reductase from Dr. Paul Killen at the University of Kansas Medical Center.

The Northern blot was prehybridized in Church's buffer for at least 1 hour prior to the addition of radio-labeled probes. The hybridization was carried out overnight at 65° C. The blot was then washed 6 times over a period of one hour. The hybridized filter was placed against a piece of X-ray film for the production of an autoradiograph.

To determine quantities of AQP2 and AQP3, Applicant employed antipeptide antibodies specific for AQP2 and AQP3. These antibodies were produced for the Applicant.

The methodology for the immunohistochemistry was described previously by Applicant. Kidneys from anesthetized (65 mg/kg sodium pentobarbital, ip) animals were frozen for cryostat sections. Sections of tissue were incubated with antisera against the protein of interest and visualized with a lissamine rhodamine labeled secondary antibody and examined with fluorescence microscopy. Controls from the immunohistochemistry included: (1) preabsorption of the antisera with the peptide or protein (if available); (2) normal rabbit or pre-immune sera rather than the antisera; and (3) sequential dilution of the antisera to identify loss of specific staining.

In nephrogenic diabetes indipidus (DI) there is a defect in either the AVP-$V_2$ receptor or AQP2 genes. In PKD-induced DI it appears that the genes of these components are not defective; however, the proteins appeared to not allow for renal concentration to occur normally. Insight from the preliminary data of Yamaji et al. (1995) suggests that after the AVP-$V_2$ receptor stimulation, the AQP2 protein does not insert into the collecting duct apical membranes as it should normally insert. In a manner similar to that of Yamaji et al., the Applicant will study AQP2 insertion into the apical membrane in thin slices of renal medulla from cystic and normal kidney incubated for 30 minutes in DMEM/F12 media with or without exogenous AVP added ($10^{-5}$M). After this, the tissue will be processed as described above for immunolocalization of AQP2 and AQP3. Additional slices will be processed for the quantification of cAMP as described above. In addition, slices of normal and cystic kidney tissue will be directly stimulated with dibutyl-cAMP (without AVP) to directly asses the ability of cAMP to stimulate apical insertion of the AQP2 protein, bypassing the step of stimulation of the AVP-$V_2$ receptor.

Cell culture studies of cystic and normal renal epithelia will be used to evaluate the regulation of AVP-$V_2$ receptor, AQP2 and AQP3 in a controlled environment. Cells were cultured from cystic and normal (3 week) renal medulla. The kidney was decapsulated, inner medulla minced and placed in a collagenase solution (Worthington Biochemicals) in a 37° C. shaking water bath for 1 hour. After the collagenase digestion, the cells are spun down at 1500× at 4° C. for 10 minutes. The cell pellet is resuspended in fresh DMEM/F12 with ITS, penicillin/streptomycin and replated in fresh DMEM/F12 with ITS, penicillin/streptomycin and the cells placed in separate 100 mm culture dishes coated with collagen type I for 24 hours for initial cell adhesion and initiation of growth. The cells were fed every 24 hours. Since previous studies have shown these cells to be epithelial, which express $V_2$ receptor and AQPs mRNA, they are assumed to be enriched for collecting duct cells.

Applicant evaluated if AVP exerts a positive feedback on collecting duct cell $V_2$ receptor and AQP expression. To a series of cultures, normal and cystic, graded doses of AVP ($10^{-9}$ to $10^{-6}$M) are added for 48 hours. Similarly, cultures may be treated with 0, 20 or 200 ng/ml of EGF, $PGE_2$ or ANP. In addition, some cultures are treated with cyst fluid to determine if a factor or cytokine from the cysts is altering the expression of these genes. After these various treatments, RNA is isolated as described above and probed for the expression of $V_2$ receptor, AQP2, AQP3 and aldose reductase (AR) mRNA.

Figure 3A:
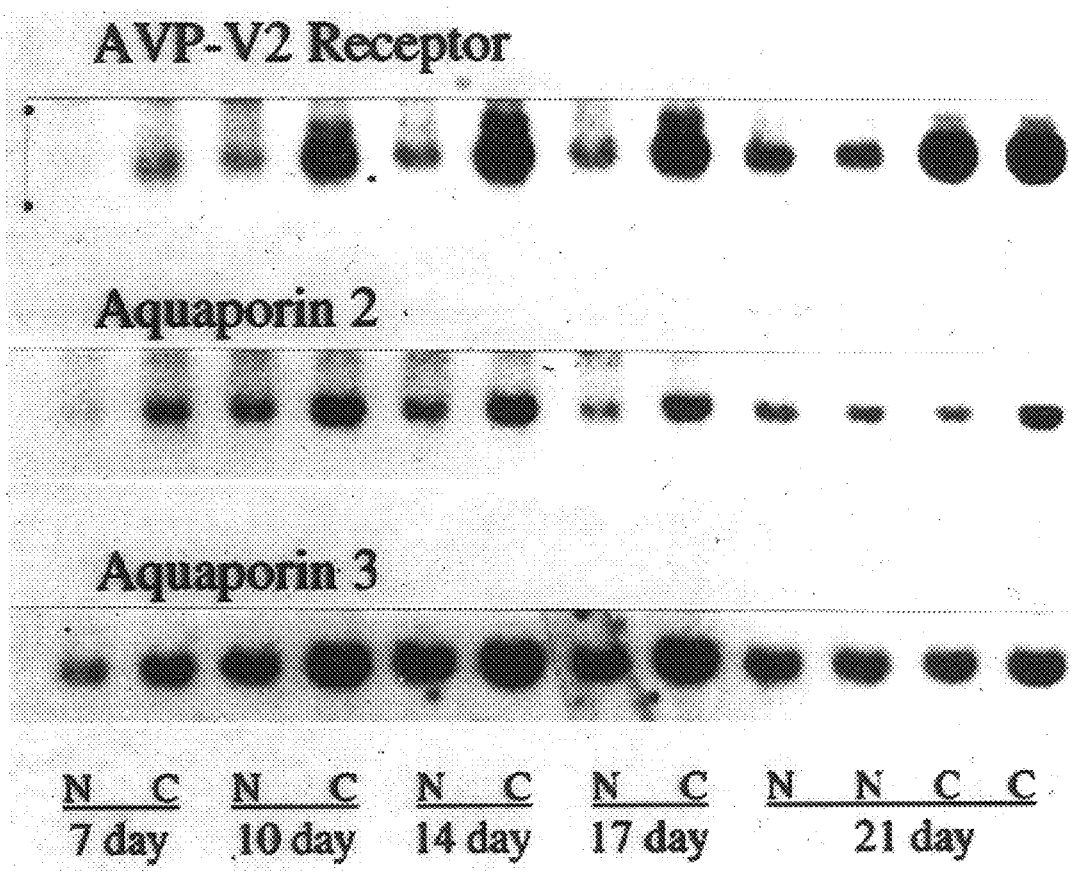
FIG. 3a is a Northern blot hybridization for mRNA expression of AVP–$V_2$ receptor, AQP2 and AQP3 in cpk cystic (C) mice and normal (N) mice at 7, 10, 14, 17 and 21 days of age.
Figure 3B:
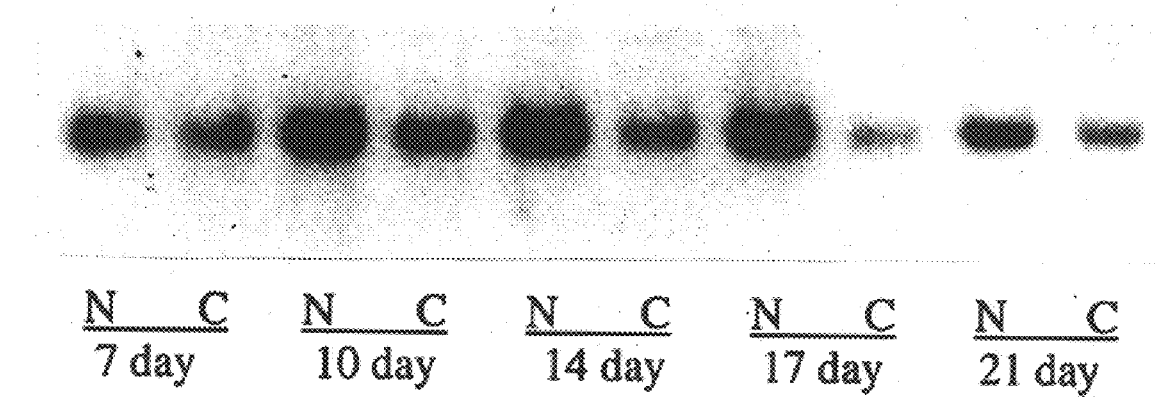
FIG. 3b is a Northern blot hybridization for mRNA expression of aldose reductase in cpk cystic (C) mice and normal (N) mice at 7, 10, 14, 17 and 21 days of age.

As shown in FIG. 3a, in cpk mice, renal mRNA expression of $V_2$ receptor, AQP2 and AQP3 was increased in cystic (C) as compared to normal (N) kidney at 7–21 days (at 21 days male and female). In normal kidney, expression of $V_2$ receptor mRNA was found to significantly increase between 7 and 21 days. In cystic kidney, there is a 2 to 4 fold increase in the expression of $V_2$ receptor mRNA at all timepoints examined, compared to normal kidney. There is a similar developmental pattern for the expression of AQP2 and AQP3 mRNA with increased expression in cystic kidney. In normal kidney, AR mRNA peaked at 10–17 days consistent with data from Schwartz et al. (*J. Clin. Invest.* 90: 1275 (1992)); however, AR mRNA was decreased suggesting a developmental delay in AR expression in cystic kidney (FIG. 3b). This is consistent with the immature phenotype of the cystic collecting duct previously described in the art and/or the lack of development of a medullary osmotic gradient. Developmental expression of $V_2$ receptor, AQP2 and AQP3 mRNA normally plateaus at 2–3 weeks. In cpk mice, CD cysts begin to form at about 7 days and the increased $V_2$ receptor, AQP2 and AQP3 may indicate their involvement in the early stages of CD cyst formation.

Figures 4A, 4B, 4C:
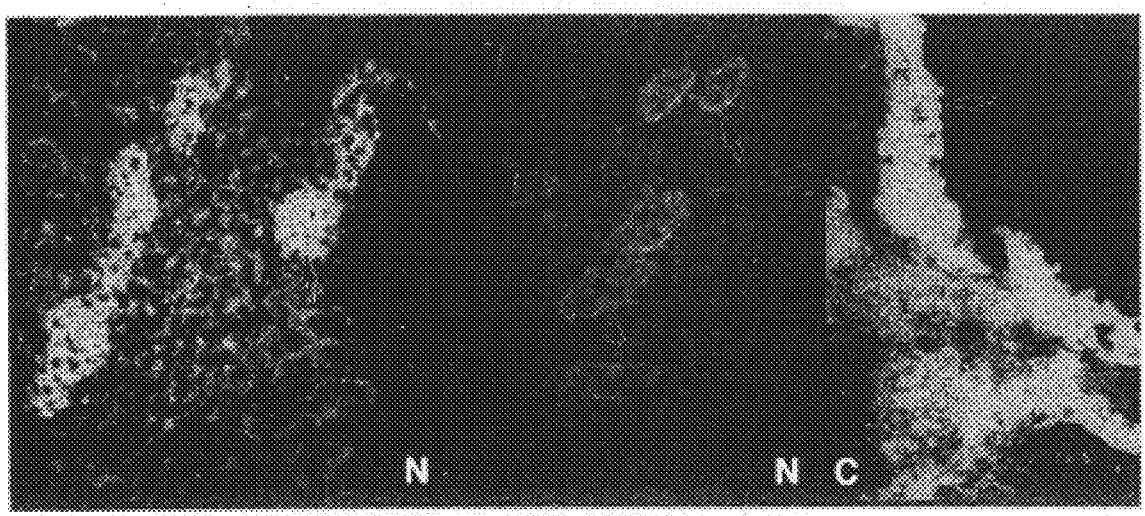
FIG. 4 is an immunofluorescence demonstration of the localization of AQP3 (a, b & c) and AQP2 (d & e). In a one week-old normal (N) mouse kidney, AQP3 can be found diffusely throughout the cells of the collecting duct (arrow in figure a). While at 3 weeks (figure b), the normal localization of AQP3 is on the basolateral aspect of the collecting duct cells (arrows). In 3 week cpk cystic kidney (C), the AQP3 is abundantly found throughout the cell (arrow in figure c). In normal 3 week kidney, AQP2 is found toward the apical side of the collecting duct epithelial cells (arrow in figure d). However, in the cystic kidney (figure e) it can be found in variable amounts and sometimes throughout the cells (arrows) rather than being isolated to the apical aspect of the cell.
Figures 4D, 4E:
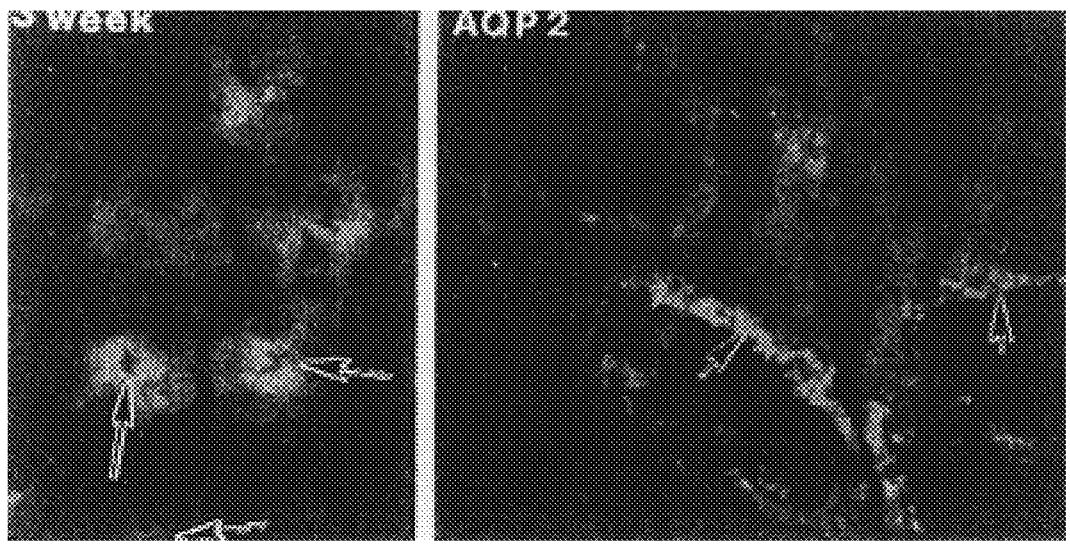

Immunohistochemistry with antibody to AQP2 and AQP3 in 3 week cpk mice shows AQP3 in the collecting ducts of 1 week normal mice and in the basolateral aspect of normal 3 week CD cells (FIGS. 4a, 4b). The cystic collecting duct cells have abundant AQP3 (FIG. 4c). AQP2 is found apically in normal CD cells (FIG. 4d); however, in cystic kidney (FIG. 4e) staining is not uniformly present in all cyst cells and typically is not found apically. These data are consistent with Northern blot hybridization data for 3 week cpk mice (FIG. 3).

A colony of C57BL/6J-cpk mice are maintained at the University of Kansas Medical Center. The colony is maintained by crossing heterozygous mice (cpk/+). Homozygous cpk/cpk mice are compared with the phenotypically normal littermates (cpk/+and +/+). The cpk mutation is found on chromosome 12 (Simon et al., 1994). This locus is not the site of mutation for human ARPKD (chromosome 6, Guay-Woodford et al., 1995). However, the cpk model is the most commonly used model for the renal pathology typically seen in human ARPKD. Entire litters were taken for examination at various timepoints. All data represent information gathered from pooled specimens comprising at least two litters containing 2–4 kidneys. Urine was collected from the urinary bladder and blood was collected from the incised right atrium of the heart from these mice after anesthesia was induced with sodium pentobarbital (65 mg/kg administered ip). Litters were used in one of four ways in Applicant's study: (a) RNA isolation to examine mRNA expression, (b) immunohistochemistry for AQP2 and AQP3 proteins, (c) treatment with a V2R receptor antagonist (OPC31260 from Otsuka Pharmaceutical Co.), or (d) for culture of the renal collecting ducts to examine mRNA expression under basal, EGF or AVP stimulated states.

a. RNA Isolation and Northern Blot Analysis

Mice were anesthetized and a laparotomy performed. The kidneys were immediately frozen in liquid nitrogen. The tissue was stored at −75° C. until processed. RNA was isolated using TriReagent (Molecular Research Center Inc., Cincinnati, Ohio) according to the manufacturer's instructions which employs a chloroform—phenol extraction methodology previously described (Gattone et al., 1995a). For each time point at least 3 mice from two different litters were pooled for Northern analysis. RNA (7 ug per lane) was electrophoresed in a formaldehyde-1% agarose gel and transferred overnight onto Zetabind (Cuno Laboratory Products, Meriden, Conn.). To assess equal loading and transfer, each membrane was stained with methylene blue and/or hybridized with a probe to 18S rRNA (Maser et al., 1994). Only membranes exhibiting roughly equivalent loading of RNA in each lane were used in this study. To assess gene expression for a number of different collecting duct or concentration associated components, blots were hybridized with specific DNA probes for rat AQP2 (described by Ma et al., 1994 and obtained from Dr. A. Verkman, UCSF, CA), rat AQP3 (nts. 297–767 isolated at KUMC by RT-PCR from rat kidney RNA; confirmed by DNA sequencing), rat AVP-V2R (obtained from Dr. Brownstein at NIMH, Bethesda, Md.; nts. 1–926 subcloned into pBluescript) and human aldose reductase (obtained from Dr. Paul Killen, University of Michigan). The specific inserts were random prime labeled with 32P-dCTP using a Rediprime kit (Amersham). Blots were hybridized for 18–20 hours at 65° C. (in 0.5M phosphate buffer, pH 7.0, 7% SDS, 1% bovine serum albumin-BSA, 1 mM EDTA solution containing the probe). The blots were washed at 65° C. for 1 hour, initially in Buffer 1 (5% SDS, 0.5% BSA, 1 mM EDTA in 40 mM phosphate buffer) then buffer 2 (1% SDS, I mM EDTA in 40 mM phosphate buffer, pH 7.0). The hybridized blots were exposed to XAR or X-OMAT XB-1 film (Kodak, Rochester, N.Y.) for the generation of autoradiographs. These probes each labeled a single major mRNA transcript (V2R—2.2 kB, AQP2—1.5 kB, AQP3—1.9 kB and aldose reductase 1.5 kB). The sizes of these transcripts are consistent that described by others transcript (V2R—Lolait et al., 1992, AQP2—Fishimi et al., 993, AQP3—Echevarria et al., 1994 and aldose reductase-Garcia-Perez et al., 1989).

b. Immunohistochemistry

Indirect immunofluorescent staining was performed as previously described (Cowley et al., 1992). Kidneys of anesthetized mice (65 mg/kg sodium pentobarbital, ip) at 7, 14 or 21 days of age were rapidly frozen in liquid nitrogen. Acetone fixed frozen sections of the kidney tissue were incubated with rabbit primary anti-peptide antisera [AQP2-peptide-immunogen was VELHSPQSLPRGSKA or AQP3-peptide-immunogen was EAENVKLAHMKHKEQ, specificity confirmed by Western analysis, data not shown] for 18 hours (at 4°). Controls for the immunohistochemistry included incubation of the sections with preimmune rabbit sera (1:100 dilution) in place of the specific antisera. Slides were rinsed in PBS and a secondary antibody conjugated with lissamine rhodamine (Jackson Immuno Research Lab, West Grove, Pa.) was incubated with the tissue sections for one hour at room temperature.

Sections were rinsed, mounted in glycerol gelatin and examined with a Nikon Labophot microscope equipped for epifluorescence.

Photographs were taken onto 400 ASA film (pushed to an ASA of 1200, Kodak Laboratories, Rochester, N.Y.).

Specificity of the antibodies was confirmed using Western blot analysis. For characterization of aquaporin antisera specificity, 25 μg of microsomal protein from 3 week old rat kidney was electrophoresed in 12.5% polyacrylamide-SDS gels and electroblotted to nitrocellulose membrane. Blots were then blocked in TBST (10 mM Tris, pH 7.4, 0.9% NaCl, 0.1% Tween 20) with 5% non-fat dry milk, incubated with antiserum or pre-immune serum at 1:1,000 dilution in TBST, washed, incubated with goat anti-rabbit IgG-alkaline phosphatase conjugate (Sigma Chemical Co., St. Louis Mo.) at 1:30,000 in TBST, washed and developed with BCIP and NBT. The antibody to AQP2 0recognized a protein band of approximately 28–31 kD not present in the preimmune sera (FIG. 3e) and the AQP3 antibody identified a similar sized protein band not seen with the preimmune sera as well.

c. Treatment of Mice

OPC31260, a V2R antagonist (Yamamura et al., 1992, Otsuka Pharmaceutical Co., Ltd., Toushima, Japan ): Whole litters of mice were either: (1) treated with OPC31260 (on days 3–7, 10 20 μl of a 10 mg/ml solution, on days 8–14, 15 μl and on days 15–21, 20 μl was injected subcutaneous, OPC31260 from Otsuka Pharmaceutical Co.), or (2) treated with comparable volumes of sterile water, or (3) given nothing. At 21 days of age (approximately 2 hours after the final injection), the mice were weighed and anesthetized. Urine (for determining osmolarity) and sera (for determining urea nitrogen levels) ere collected. The kidneys were weighed after which one was sliced and fixed in 10% buffered formalin. Segments of the fixed kidney were processed for standard paraffin histology. The relative volume (Vv-volume density) of cyst within the kidney was determined using point count stereology. The other kidney was processed for RNA isolation and Northern blot hybridization as described above.

EGF treatment: These specimens were derived from a previous published study (Gattone et al., 1995a) in which whole litters were treated with lug/g body of EGF from days 3–9. RNA isolated from those mice was subjected to electrophoresis, blotted and hybridized as described above.

d. Primary Cultures of Normal and Cystic Renal Epithelia

Normal and cystic renal epithelia were cultured as described by Rankin et al. (1992). Mice were euthanitized with an overdose of sodium pentobarbital (200 mg/kg) and when respiration ceased, the mice were dipped in 95% ethanol and placed inside the culture hood. The medulla was removed from normal kidneys and minced prior to incubation in DMEM/F12 culture media containing collagenase (type 1, Worthington Biochemical Co.) for 2 hours at 37° C. Minced cystic kidney was incubated in the same collagenase solution for 2.5 hours. The resulting cellular material was centrifuged at 5000 g for 5 minutes and the pellets were resuspended in fresh CellGrow Media (Mediatech Inc., Hemden, Va.) with ITS and penicillin/streptomycin and plated onto T75 plates coated with collagen type I (Collaborative Research, Bedford, Mass.). After 24 hours, the cells growing on the plate were released using cell dissociation solution (Sigma Chemical Co., St. Louis, Mo.) and $5 \times 10^6$ cells were plated into fresh T75 plates incubated in the same medium except with: (1) 0, $10^{-9}$ or $10^{-6}$M AVP, or (2) 0, 20 or 200 ng/ml EGF, added to the medium. RNA was isolated from these cultured cells and Northern blot hybridizations were carried out as described above.

Data Analysis.

Data was compared using an analysis of variance with a $p<0.05$ indicating significance.

e. Results in cpk Model

Figure 7A:
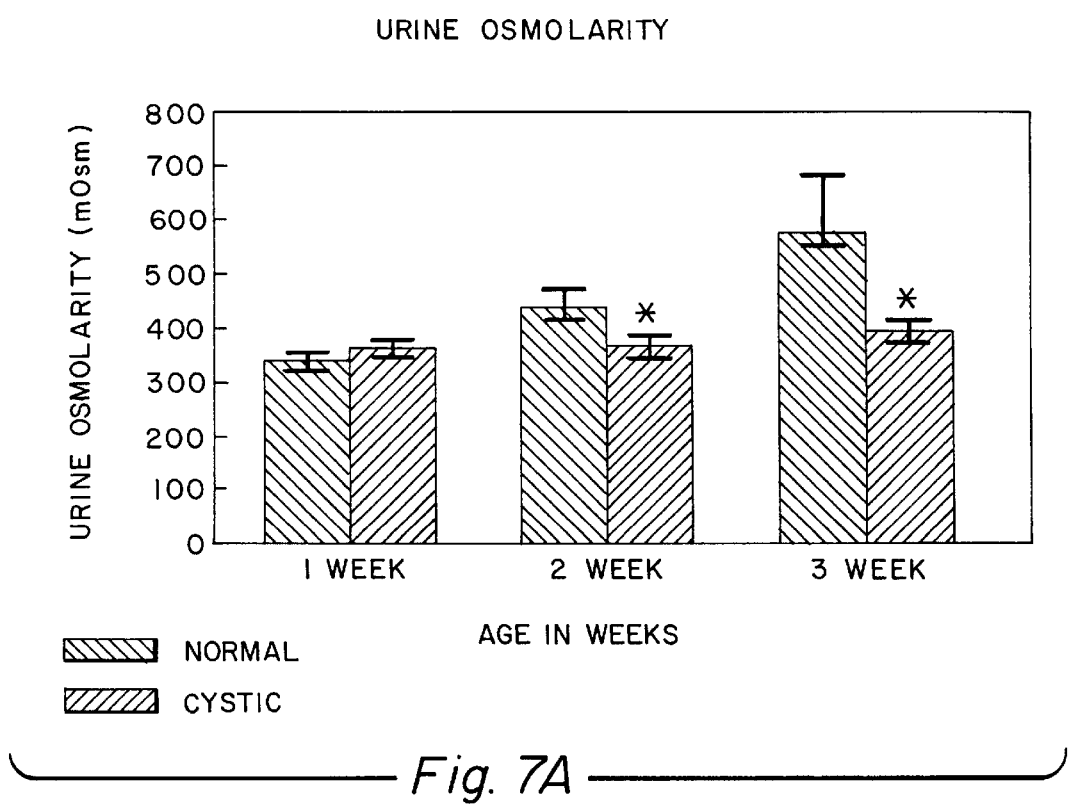
FIG. 7a is a bar graph illustrating that urine osmolarity in non-dehydrated mouse pups steadily increases from 1 through 3 weeks of age. However, in the cpk cystic mice, the urine osmolarity did not increase with age and had a significantly lower osmolarity than normal pups at two and three weeks of age.
Figure 7B:
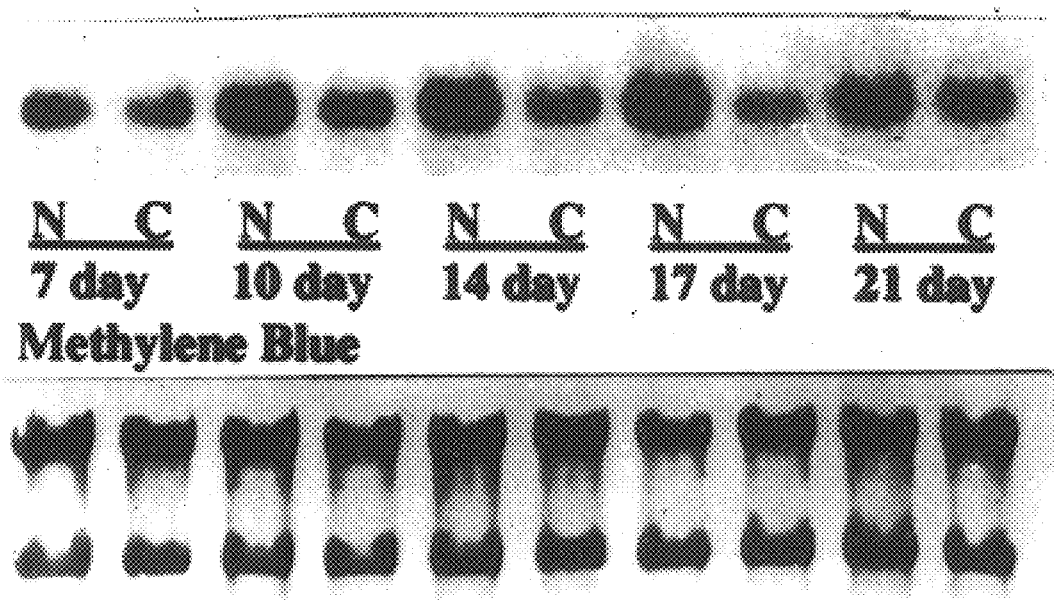
FIG. 7b is a Northern blot hybridization for aldose reductase mRNA expression illustrating an increased expression in normal mice during the developmental period from 7–17 postnatal day and then assumes a steady state level of expression. However, in cpk cystic mice there is no increase in aldose reductase mRNA expression during this period suggesting that the medulla never develops a hypertonic interstitium. The decrease in expression in normal kidney seen between 17 and 21 days reflects the overall decrease in the relative amount of medulla (where aldose reductase is expressed) compared with the increase in renal cortex development. Methylene blue staining of the blot (pictured at the bottom of the figure) prior to hybridization indicated a similar amount of total renal RNA in each lane.

The development of urinary concentrating capability in normal and affected mice was examined by determining urinary osmolarity. In phenotypically normal mice urinary osmolarity increased during the early postnatal period (FIG. 7a). However, in cystic mice, the urinary osmolarity was similar to that of the one week-old normal mice and did not change over this period of time. There is a developmental increase in renal aldose reductase mRNA in normal mouse kidney, becoming maximal at 17 days of age (FIG. 7b). Aldose reductase is responsible for the generation of sorbital, an osmolite which renal cells use to protect themselves from the hypertonic environment of the medulla. In the cpk cystic kidney, the steady state aldose reductase mRNA levels fail to increase comparable to normal kidney mRNA levels (FIG. 7b). This finding suggests that cystic kidneys lack a medullary concentrating gradient which would certainly contribute to the renal concentrating defect of the cystic kidney. At present, it is unclear why this gradient may fail to develop. The thick ascending limb which is responsible for generating this gradient is already known to have a developmental delay in preproEGF expression (Gattone et al., 1990). Alternatively, the collecting duct immaturity as suggested by the data of Harding et al. (1991) may also contribute to this problem in the cystic kidney.

Figure 8:
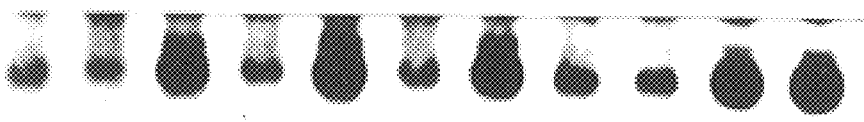
FIG. 8. Developmental expression of urine concentration-associated genes in normal and cystic kidney. Expression of the V2R, AQP2 and AQP3 all increase in the normal mouse kidney during this initial 2–3 postnatal weeks of life. However, the cpk cystic kidney has a higher expression of these same mRNAs starting at or before 7 days of age. This early increase in expression cannot be explained solely by a increased amount of collecting ducts cell (cysts) since there are very few cysts present at 7–10 days of age. Note that the V2R mRNA overexpression remains at 21 days while there is only minimal overexpression of AQP2 and AQP3 at this time. Methylene blue staining of the blot prior to hybridization and hybridization with a probe for 18S rRNA (both pictured at the bottom of the figure) indicated that all lanes had a similar amount of total renal RNA.
Figure 8:
Figure 8:
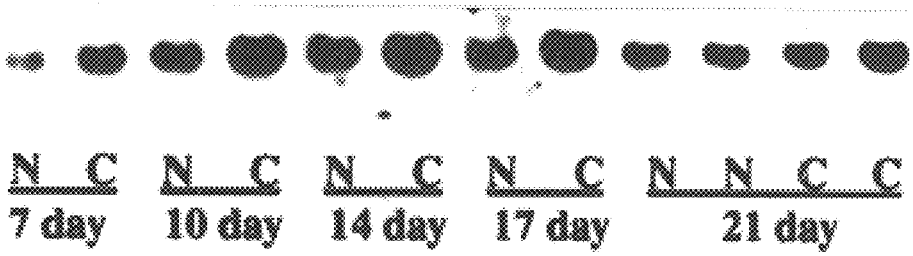
Figure 8:
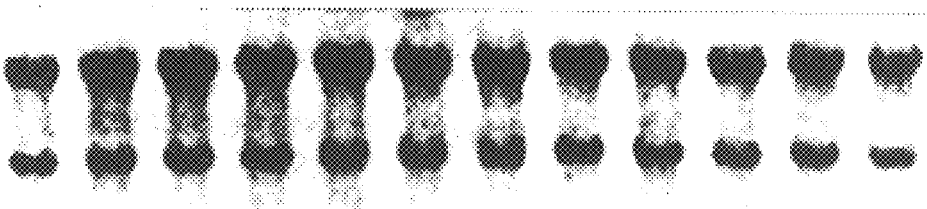
Figure 8:

To determine if an altered state of collecting duct differentiation contributes to the inability of the cystic kidney to concentrate urine, Applicant examined the steady-state expression of AVP-V2R, AQP2 and AQP3 mRNAs in vivo. Messenger RNAs for these three collecting duct genes were expressed at least as early as 7 days of age and reached maximal levels at 14–17 days of age (FIG. 8). The increasing expression of these genes appears to correlate with s the development of hypertonic urine. There was an overexpression of AVP-V2R, AQP2 and AQP3 mRNAs in the cystic kidney at all time points examined (FIG. 8). Therefore, the overexpression of collecting duct concentration-associated genes in PKD preceded both significant collecting duct cyst development and the development of azotemia in cpk mice (Gattone et al., 1987).

Figure 9A:
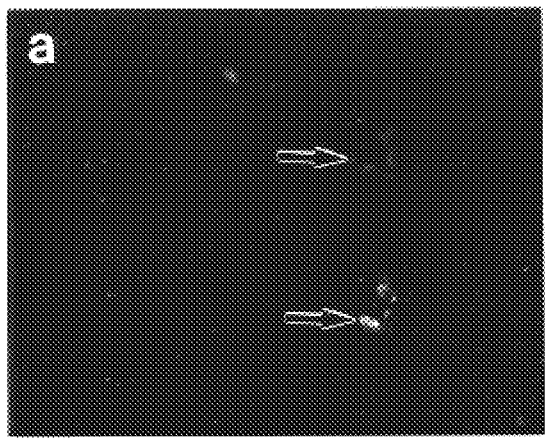
FIG. 9. Aquaporin 2 and 3 immunohistochemistry of the kidney. Aquaporin 2 staining of the 3 week normal (a) and cpk cystic (b) kidney shows staining of the apical portion of the collecting ducts cells in normal kidney however, in the cystic kidney the staining is variable between cysts and is nor always along the apical part of the cell. Aquaporin 3 staining of 3 week normal (c) and cystic (d) kidney shows basolateral staining in normal collecting ducts with variable basolateral staining of the cystic epithelium. 175× (e) Western blots analysis showing the specificity of the AQP2 and AQP3 antisera for a 28–31 kD protein in a kidney microsome preparation. The comparisons are to the preimmune sera.
Figure 9B:
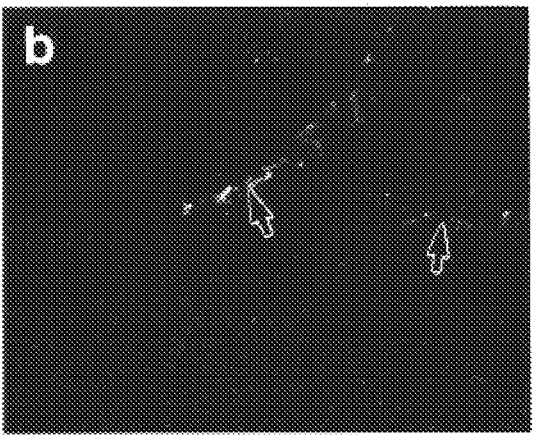
Figure 9C:
Figure 9D:
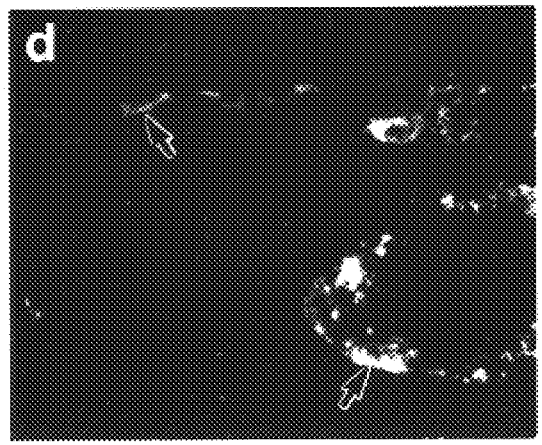

In normal kidney, AQP2 is mainly found in the apical portion of the cells. However, in the cystic collecting duct, AQP2 was generally present throughout the cell (FIG. 9a versus b) suggesting a misregulation of the sorting or insertion of this water channel. Applicant findings confirm the cellular localization of AQP2 previously described in cpk kidney by Aziz et al. (1996). AQP3 is present basolaterally in normal kidney and in most cystic collecting duct cells (FIG. 9c & d). At 3 weeks of age, large cysts appear to have decreased amounts of aquaporins compared with smaller cysts and normal-appearing collecting ducts.

Figure 10A:
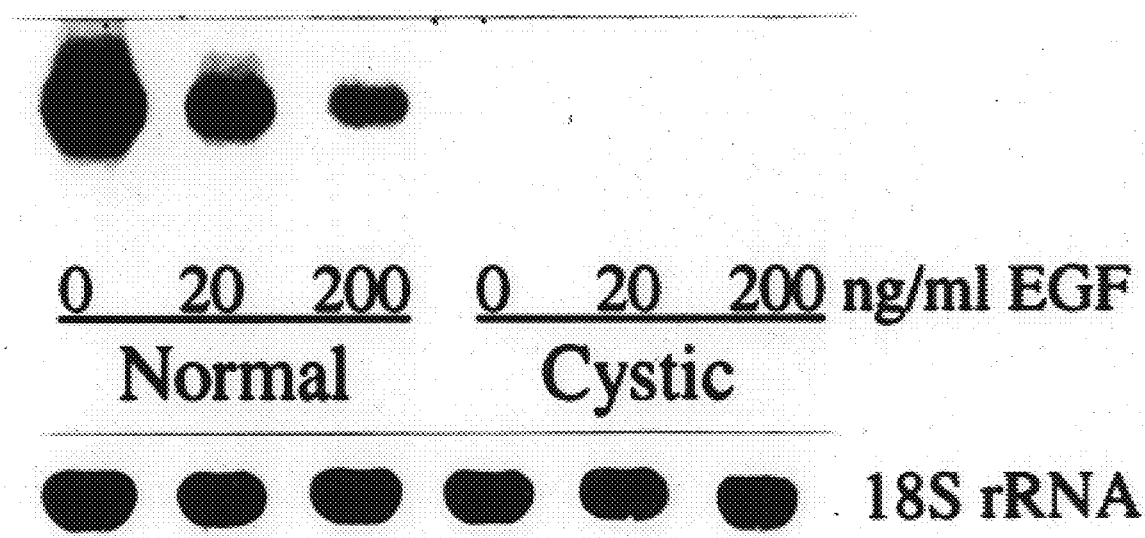
FIG. 10. Effect of EGF on expression of the urine concentration-associated genes. A. EGF downregulates the expression of V2R mRNA in normal primary collecting duct cultures. However, there was minimal expression of the V2R by the cultured cpk cystic collecting duct cells. Hybridization with a probe for 18S rRNA (at bottom of figure) showed that this pattern of expression was not related to any differences in the amount of RNA present in each lane. B. EGF treatment on days 3–9 which partially ameliorated the PKD in cpk mice (Gattone et al., 1995a) increased the expression of these concentration-associated genes in 2 week-old normal and cystic mice, however, there was little evidence of an EGF effect remaining at three weeks of age. Methylene blue staining of the blot prior to hybridization (at bottom of figure) show the amount of total RNA.
Figure 10B:
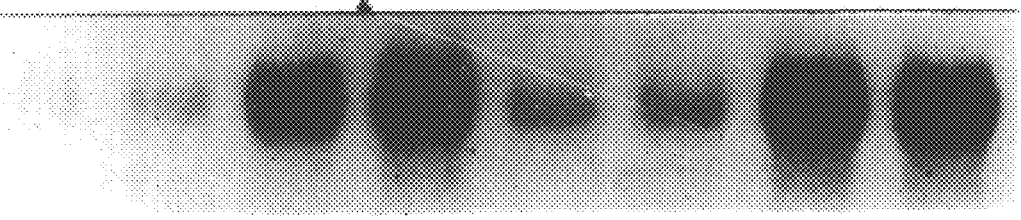
Figure 10B:
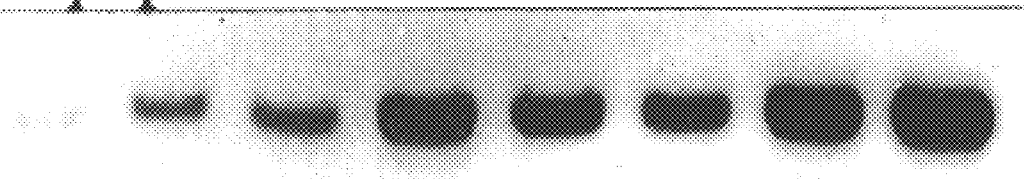
Figure 10B:
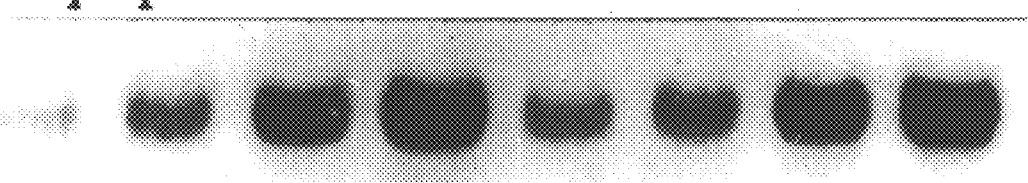
Figure 10B:
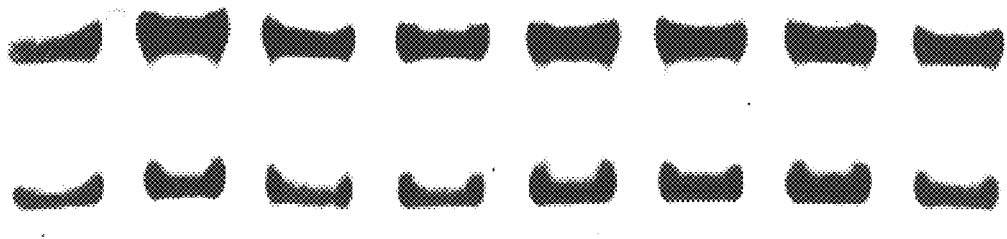

The overexpression of V2R and AQPs by the cystic kidney may represent a response to an abnormal humoral environment in vivo. Expression of EGF is virtually absent in the cpk cystic kidney (Gattone et al., 1990, Horikoshi et al., 1991). EGF repletion ameliorates the PKD in cpk mice suggesting that the lack of EGF contributes to the cystic renal changes (Gattone et al., 1995a). EGF is known to influence V2R activity (Breyers et al., 1988, Phillips et al., 1994). In normal collecting duct cultures, EGF treatment decreased the expression of the V2R mRNA in a dose dependent manner (FIG. 10a) however cultures of cystic epithelia exhibit very low levels of expression. This suggests that the lack of EGF in cpk mice might permit the overexpression of the V2R gene in vivo. To evaluate this hypothesis renal RNA from normal and cystic mice treated with EGF from days 3–9 was isolated and examined on days 14 or 21 for the expression of these CD genes. At 2 weeks of age, the EGF treated normal and cystic mice appeared to have an increased renal expression of V2R, AQP2 and AQP3 mRNAs (FIG. 10b). By 3 weeks, there was no discernible difference associated with EGF treatment in either normal or cystic kidney. Based upon these EGF treatment studies, the lack of EGF in the cystic kidney does not appear to contribute to the overexpression of the V2R mRNA in the cpk mouse in vivo.

Figure 11:
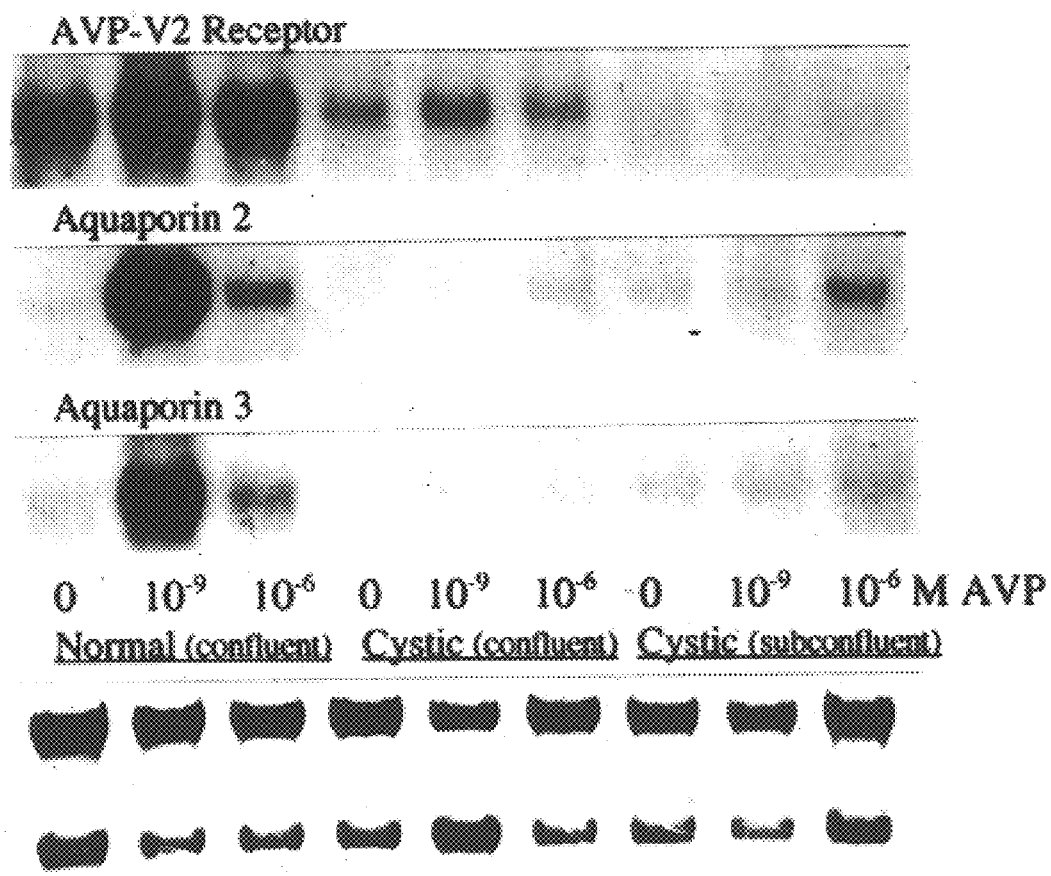
FIG. 11. Effect of AVP on expression of the urine concentration-associated genes by cultured cells. Normal medullary collecting duct epithelia grown in media containing AVP at physiological levels ($10^{-9}$M) exhibited an increased expression of V2R, AQP2 and AQP3 mRNA. A higher concentration ($10^{-6}$M) blunted that overexpression slightly for the V2R mRNA but markedly for AQP2 and AQP3 mRNAs in these confluent cultures of normal cells. Cultures of cpk cystic epithelial cells had a much lower level of mRNA expression for these mRNA which made it difficult to evaluate the effects of AVP. While there appeared to be relatively little effect on the expression of the V2R mRNA, the higher concentrations of AVP appeared to increase the expression of AQP2 and AQP3 in both the confluent and subconfluent cultures. Note that the subconfluent culture of cystic cells had a lower expression of V2R mRNA than did the confluent cultures. It is thought that this might represent a maturational change associated with reaching confluence. Methylene blue staining of the blot prior to hybridization (shown at the bottom of the figure) indicate that all lanes had approximately the same amount of total RNA.

It is also possible that increased AVP stimulation contributes to the increased renal expression of the concentration-associated genes. To assess the possible influence of AVP on collecting duct gene expression: (a) normal and cystic collecting duct cell primary cultures were treated with AVP, and (b) normal and cystic mice were treated with an AVP-V2 receptor antagonist. When physiological amounts of AVP ($10^{-9}$M) were added to the culture medium, confluent normal collecting duct cells exhibited an increased steady state expression of the V2R, AQP2 and AQP3 mRNAs (FIG. 11). Supraphysiological levels of AVP ($10^{-6}$M) partially downregulated this overexpression by normal cells. The lower level of mRNA expression for concentration-associated genes by the cultured cystic epithelial cells made it difficult to determine if a similar stimulation occurred in those cells. However, it appears that the higher concentration of AVP was necessary to generate an increased expression of AQP2 in cystic epithelial cultures suggesting that these cells have a diminished responsiveness to AVP (FIG. 11). Interestingly, the expression of V2R mRNA was lower in the subconfluent cultures of cpk cystic epithelia, which altogether suggests a general immaturity of the cystic epithelial cells that is further accentuated in subconfluent cultures.

Figure 12:
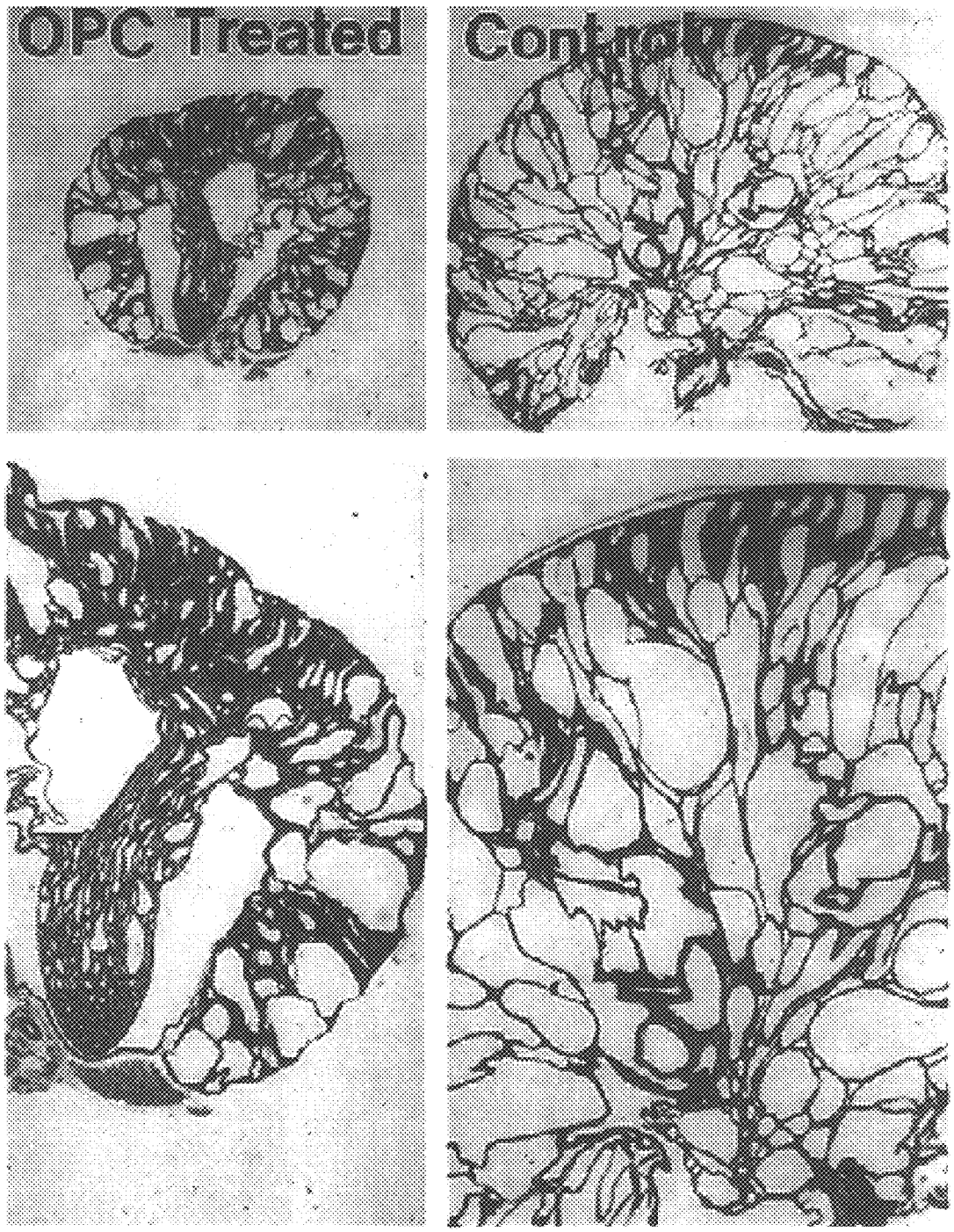
FIG. 12. Histology of the effects OPC31260 treatment on the cpk kidney. At three weeks the untreated cpk kidney is composed almost entirely of large collecting duct cysts (right panels), however, in cpk mice treated with OPC31260 the cysts appear to be smaller and more functional parenchyma appears to be present (left panels).
Figure 13:
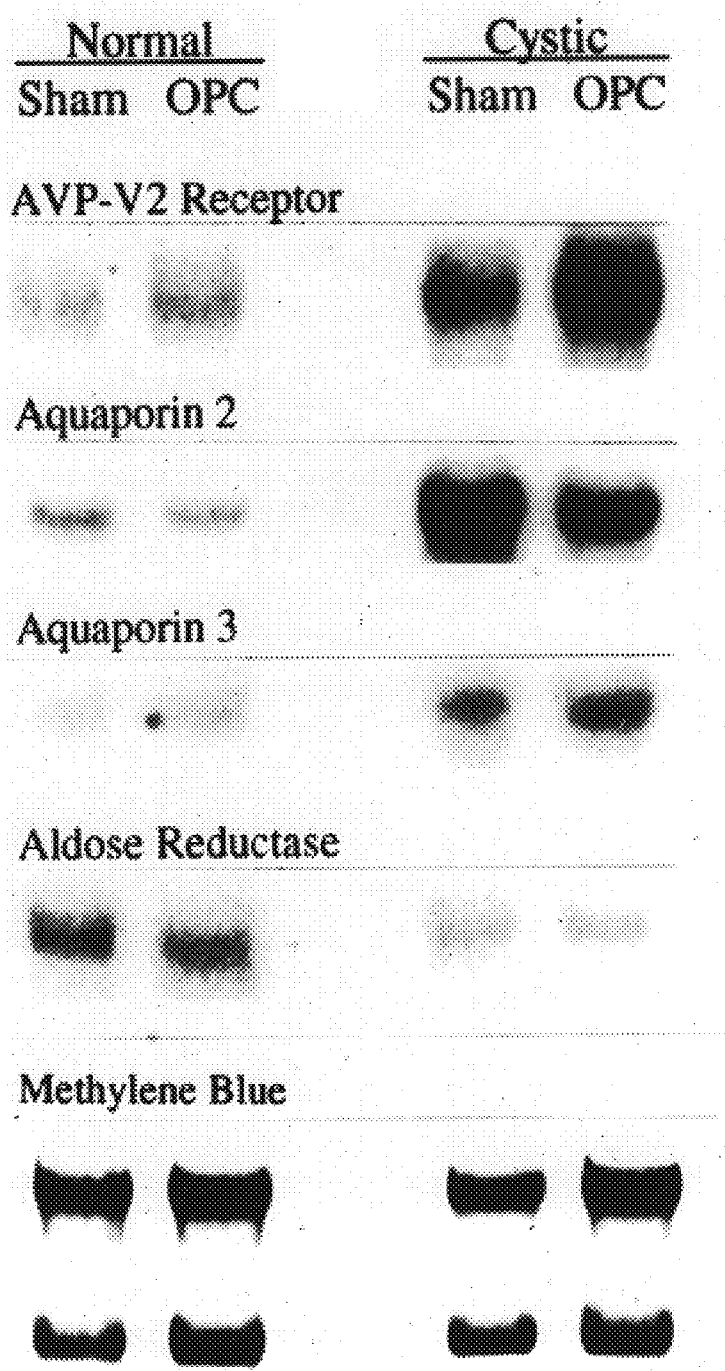
FIG. 13. Effect of OPC31260 treatment on the in vivo expression of urine concentration-associated genes. OPC31260 treatment was associated with a decrease in AQP2 mRNA expression which likely reflects the lower cAMP levels expected from blocking V2R activity by this antagonist. Methylene blue staining of the blot prior to hybridization indicate the total renal RNA loaded into each lane.

Treatment of cpk mice with the V2R antagonist, OPC31260 partially ameliorated the cystic disease (reduced renal enlargement, cystic change and serum urea nitrogen, Table 1, below and FIG. 12). This finding implicates AVP activation of the V2R and the subsequent stimulation of renal cAMP in the promotion of cystic enlargement in murine ARPKD. With treatment, normal mice produced hypotonic urine, however, there was minimal effect on urine osmolarity in the treated cystic mice since their urine was already more dilute. Compared with sham-treated controls, OPC31260 treatment appears to have increased the mRNA expression of the AVP-V2R (FIG. 13). This suggests that AVP stimulation of the V2 receptor should normally downregulate the expression of V2R mRNA and in the absence of that inhibitory effect, V2R mRNA expression increases. The decreased expression of AQP2 mRNA is consistent with an inhibition of V2R activity since cAMP from activated V2R normally upregulates expression of this mRNA. Treatment did not appear to change aldose reductase or AQP3 mRNA expression in either normal or cystic kidney nor the phenotype associated difference (FIG. 13). The reduced severity of PKD in OPC31260-treated mice suggests a role for cAMP in the progression of the cystic change. At present, the exact mechanism resulting in the elevated expression of V2R and AQP mRNAs in the cystic kidney is unclear.

In the present study Applicant examined the expression of mRNA for four genes associated with urine concentration. The increased expression of aldose reductase in normal mice confirms the findings of Schwartz et al. (1992) which appears to be closely linked to the development of a hypertonic medulla and the ability to concentrate urine. The expression of the V2R, AQP2 and AQP3 mRNAs in the developing mouse kidney similarly increased during the time period when urine concentration capability is normally seen. One might expect then that in PKD, where the cystic epithelia has been considered to exhibit an immature phenotype, that the lack of renal concentration capability would be due to a reduction in the expression of these critical proteins. However, this study demonstrates extensive and surprising misregulation of these gene products.

In the cpk cystic kidney, the expression of aldose reductase does not increase with age suggesting that the medulla fails to generate a hypertonic interstitium. This lack of a hypertonic medulla, probably more than any other change, is critical to the inability of the cystic kidney to concentrate urine. The cause of this inability to generate/maintain a hypertonic medulla is not known; however, it could stem from the structural distortion of the medulla and medullary circulation by developing cysts, or from an inability of the thick ascending limb to generate a gradient. It does not appear to result from the lack of collecting duct expression of the genes involved in urine concentration.

Contrary to expectations, the mRNAs for V2R, AQP2 and AQP3 were all overexpressed in the cystic kidney, even at 7 days when there are very few collecting duct cysts. At the latest timepoint examined, when the kidney is comprised almost exclusively of collecting duct cysts, the expression of the AQP mRNAs is only slightly increased. This may be explained by the apparently disparate AQP2 and AQP3 staining between smaller and larger cysts. The larger cysts appear to have less prominent staining than smaller cysts, suggesting that the epithelia from larger cysts may have reverted to a more immature or altered phenotype. The AQP2 appears to have lost some of its polar localization in the cystic epithelial cells consistent with the data of Aziz et al. (1996) in cpk mice and as seen in a minority of CD cysts in human ADPKD (Hayashi et al., 1997). Hayashi et al. (1997) also describe less prominent AQP2 and AQP3 staining in those ADPKD cysts with the loss of polarization. In contrast to Applicant's in vivo observations, a lower expression of these concentration associated genes in the cpk kidney was evident when cystic epithelial cells were grown in culture. In culture, cpk cystic epithelial cells express some mRNAs in a similar manner to what was seen in vivo, including increased SPG-2, c-fos, collagen types I and IV, fibronectin and MMP-2 mRNA (Taub et al., 1990, Harding et al., 1991, Gattone et al., 1995b, Rankin et al., 1996, Rankin et al., 1999). However, the decreased V2R, AQP2, and AQP3 mRNA expression seen in vitro was not consistent with the generally increased expression seen in vivo. The in vitro results may reflect the immaturity of the collecting duct epithelial cells in the absence of any humoral, in situ effects.

Humoral factors play an important part in regulating renal collecting duct differentiation and have been shown to play an important role in regulating the progression of rodent PKD (testosterone, Cowley et al., 1997). In the cpk kidney, preproEGF expression is severely diminished and EGF can inhibit AVP–V2 receptor activity ex vivo (Breyer et al., 1988). The present study additionally found that EGF can downregulate the expression of V2R mRNA in vitro. Therefore, it would be reasonable to postulate that the absence of EGF in the cpk mouse might contribute to the overexpression of V2R mRNA. However, this does not appear to be the case since in vivo treatment with EGF sufficient to ameliorate the PKD (Gattone et al., 1995a) was not associated with a downregulation of the overexpressed mRNAs at 2 weeks of age, but rather with an increased expression of these urine concentration-associated genes in both treated normal and cystic mice. These findings suggest that extrapolation of culture results to the in vivo situation must be done cautiously. The response of a target tissue to a humoral agent in vivo may represent both a direct effect but also the secondary effects due to its actions on associated and interacting cells, whereas, in culture the effect is solely on the target cells of interest.

Figure 5:
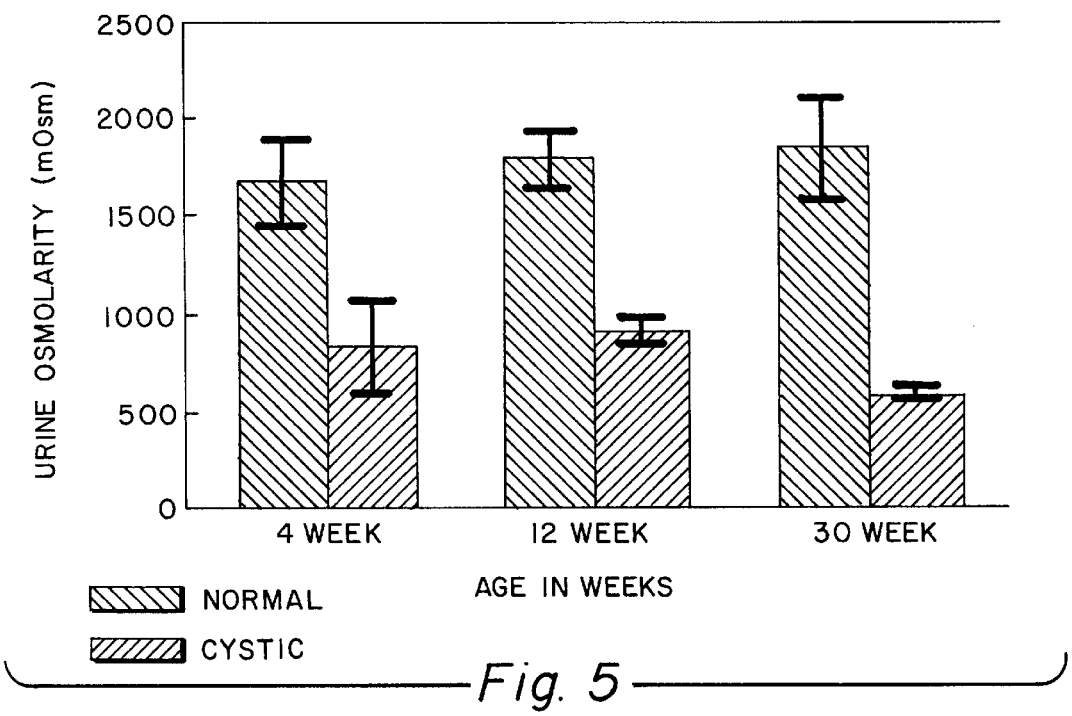
FIG. 5 is a bar graph illustrating urinary osmolarity in pcy mice from 4 to 30 weeks of age as compared to normal mice.

Dehydration (Saito et al., 1997) in vivo and AVP (FIG. 5) in vitro stimulate the expression of these urine concentration-associated genes, however, AVP is also known to acutely downregulate expression of the AVP–V2 receptor in vivo (Terashima et al., 1998). Therefore, it is unclear whether inhibition of the V2R with a receptor antagonist would be expected to increase or decrease expression of these mRNAs. While OPC31260 (a specific, non-peptidergic AVP–V2R antagonist) treatment reduced the steady state mRNA level for AQP2 (consistent with an inhibition of cAMP generation), the expression of V2R appears to be increased. This suggests that AVP stimulation of V2R has two distinct actions, the first activity being the heteromeric G-protein-related activation of adenylyl cyclase (with the cAMP stimulating AQP2 mRNA expression) and a second activity being to decrease the expression of V2R mRNA as described by Terashima et al., (1998). OPC31260 appears to effectively inhibit both of these AVP functions. In addition, stimulation of adenylyl cyclase with its subsequent cAMP production appears to contribute to the progression of the renal cystic disease since OPC31260 partially ameliorates the severity of PKD in this cpk model. This finding supports the in vitro ability of cAMP to accelerate the growth of cysts (Mangoo-Karim et al., 1988). The additional importance of this latter observation is that while no treatment is yet available to prevent the development of PKD, one therapeutic approach is to interrupt those pathways contributing to the progression of the disease.

3. Pcy Model

Mice homozygous for the pcy gene develop a slowly progressive form of PKD which closely resembles human ADPKD. Renal cysts develop in many different tubule segments and cause moderate to severe renal insufficiency by 8 months of age. Takahashi et al. (1991). The PKD research group at University of Kansas Medical Center maintains breeding colonies for various inherited models of PKD, including the CD1-pcy/pcy mouse model. Pcy/pcy mice were obtained by breeding homozygotes. Normal CD1 served as controls.

Urine was collected for assessing osmolarity. Blood for serum arginine vasopressin determination was collected by decapitating the mice and collecting the blood in heparinized tubes. If AVP levels were not needed on a group of mice, they were anesthetized with sodium pentobarbital (65 mg/kg, intraperitoneal) prior to the collection of tissues. The kidneys were then rapidly removed and processed for one of several different evaluations. Body weight and kidney weight was determined. Kidney tissue was processed for either: morphology (immersion fixed in 4% paraformaldehyde in 0.1 M phosphate buffer), or homogenized in TriReagent (Cincinnati, Ohio) for isolation of RNA.

Examination of Structural Distortion of Kidney and Determination of Medullary Osmolarity Urine osmolarity was determined by a Wescor vapor pressure osmometer without a period of dehydration from cystic mice and compared with normal mice similarly treated. Urine osmolarity was decreased in the pcy mouse at all timepoints examined (4 weeks of age through 30 weeks, FIG. 5). Urine osmolarity will be correlated to the osmolarity of the inner medulla of mice. To determine structural distortion, a section of the contralateral kidney (cortex through inner medulla) is fixed and processed for histology. The volume density (Vv) of cysts in cortex, outer medulla and inner medulla were determined as previously described (Gattone et al., 1995) using point count stereology. These evaluations will be performed on cystic and normal mice at all time points under study. Urine osmolarity, medullary osmolarity and structural distortion by cysts—Vv of cysts will be evaluated using analysis of variance.

Determination of Serum Vasopressin

Plasma vasopressin was determined using a radioimmunassay method (Kadekaro et al., 1995). This determination was made for 30-week cystic and normal mice (4 samples each, sera pooled from 2 mice for each sample). Samples were pooled because one ml of plasma was needed for a determination using the method of Kadekaro et al. (1995). These assays were performed in conjunction with Dr. Joan Summy-Long in the Department of Pharmacology at the Hershey Medical Center, Pennsylvania State University. In 30 week pcy cystic mice, the serum vasopressin levels were elevated (796±66 pg/ml) compared to 30 week normal mice (494±23 pg/ml).

Expression of $V_2$ Receptor, AQP2, AQP3 and AR Expression in pcy and Normal Kidney RNA was isolated from the kidneys of 4, 12 and 30 week CD1 and CD1-pcy/pcy mice in the same manner as described above for the cpk model. Applicant obtained nucleic acid probes and the Northern blot were hybridized as previously described.

Fifteen residue peptides specific for AQP2 and AQP3 have already been identified and the immunization of two rabbits per peptide was carried out for the production of a polyclonal antibody. Antibodies to ANP and EGF were purchased from Pennisula Labs, Belmont, Calif., as were the cAMP radioimmunoassay (RIA) kits. The antibody to PGE2 was requested from Dr. T. J. Parkinson (Univ. of Nottingham) and was used as described by Cheng et al., (1993).

Kidneys from anesthetized (65 mg/kg sodium pentobarbital, intraperitoneal) animals were frozen for cryostat sections. Sections of tissue are incubated with antisera against the protein of interest and visualized with a lissamine rhodamine labeled secondary antibody and examined with fluorescence microscopy. Controls for the immunohistochemistry are described above. AVP $V_2$ receptors will be quantified and localized as described above. Urinary and renal medullary cAMP levels will be quantified using an RIA kit from Pennisula Labs. Cells were cultured from cystic and normal (4 week) kidney as described above.

Figure 6A:
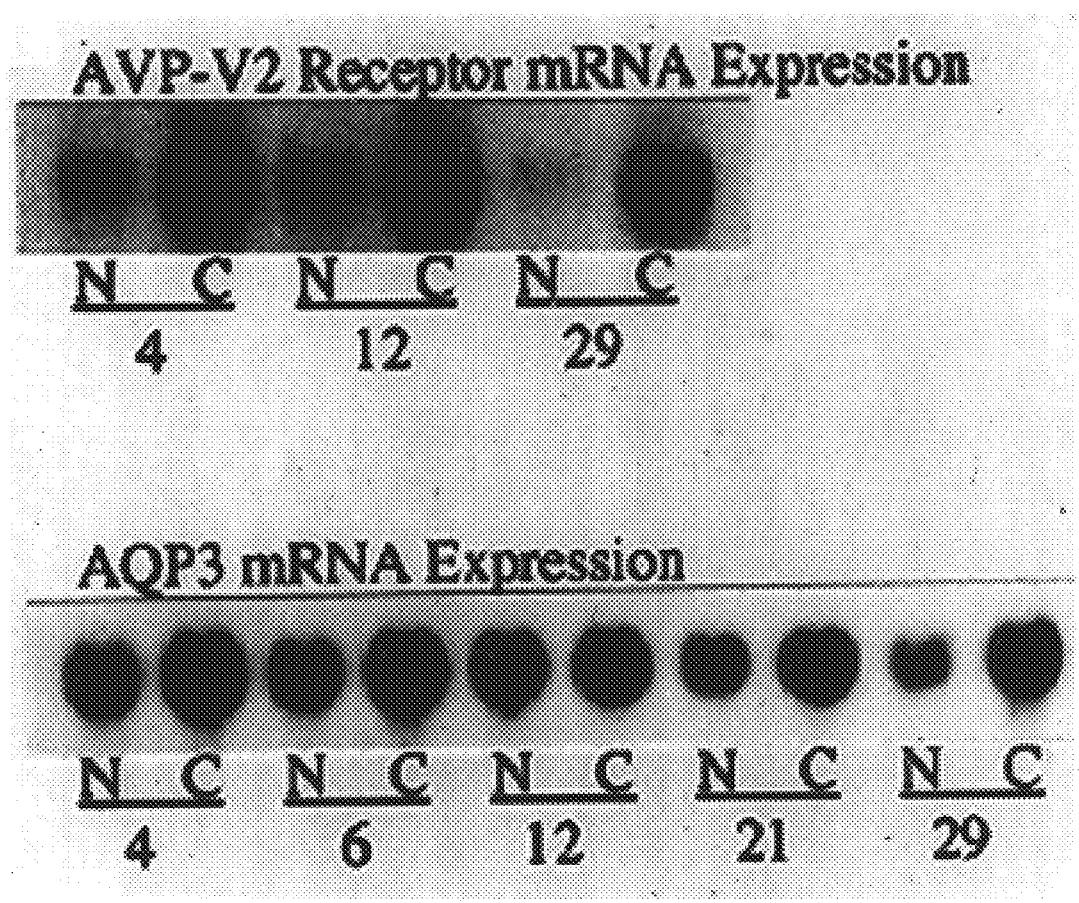
FIG. 6a is a Northern blot hybridization for mRNA expression of AVP–$V_2$ receptor and AQP3 in pcy cystic (C) mice and normal (N) mice at 4, 12 and 29 weeks of age for AVP–$V_2$ receptor expression and 4, 6, 12, 21 and 29 weeks of age for AQP3 expression.
Figure 6B:
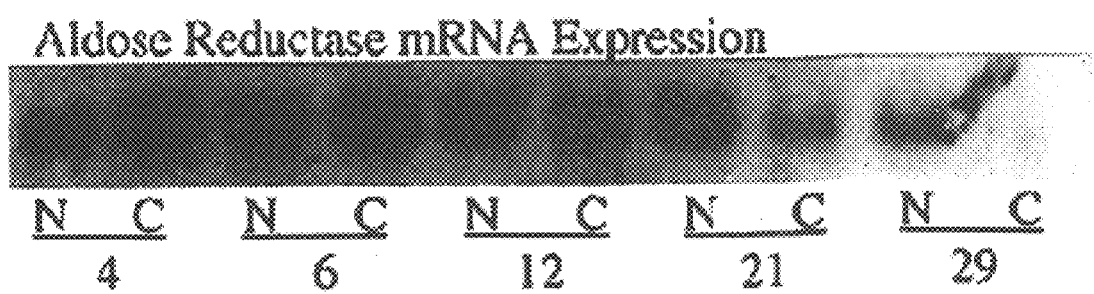
FIG. 6b is a Northern blot hybridization for mRNA expression of aldose reductase in pcy cystic (C) mice and normal (N) mice at 4, 6, 12, 21 and 29 weeks of age.

In pcy mice, as illustrated in FIG. 6a, $V_2$ receptor and AQP3 mRNAs were increased in cystic (C) kidney at 4–29 weeks of age as compared to normal (N) kidney. Expression of $V_2$ receptor and AQP3 is significantly increased in cystic kidney at all timepoints examined. Expression in normal kidney decreases with age while the expression in cystic kidney remains equivalent throughout the study period. The expression of AR is elevated early in cystic kidney but decreased later suggesting medullary washout occurred after 12 weeks (FIG. 6b).

Thus, $V_2$ receptor, AQP2 and AQP3 mRNAs were increased while AR mRNA was decreased in both adult and infantile forms of PKD.

B. Use of $V_2$ Receptor Antagonist to Treat PKD

Based on the above results demonstrating overexpression of the AVP-$V_2$ receptor in PKD, Applicant postulated that cellular cAMP is probably elevated which could promote cyst enlargement. To test this theory, cpk and pcy mice were administered a $V_2$ receptor antagonist, OPC-31260 [5-dimethylamino-1-{4-(2-methylbenzoylamino)benzoyl}-2, 3,4,5-tetrahydro-1 H-benzazepine] obtained from Otsuka Pharmaceutical Co. See Yamamura et al., Characterization of a Novel Aquaretic Agent, OPC-31260, as an Orally Effective, Nonpeptide Vasopressin $V_2$ Receptor Antagonist, BRITISH J. PHARM., 105: 787–91 (1992).

Cpk and control mice were studied at 21 days of age. Cpk mice are obtained by breeding heterozygotes. Approximately 25% of their offspring will have a cpk genotype, the cystic phenotype. Urine was collected by the method of Kavlock & Gray (1982). Blood for serum urea nitrogen was collected for determination of renal function. The kidneys of anesthetized mice were rapidly removed for several different evaluations. Body weight and kidney weight were determined. Kidney tissue was processed for either: (1) morphology (immersion fixed in 4% paraformaldehyde in 0.1M phosphate buffer) or (2) kidney homogenized in TriReagent (Cincinnati, Ohio) for the isolation of RNA.

Urine osmolarity was determined by a Wescor vapor pressure osmometer. To determine structural distortion, a section of the contralateral kidney (cortex through inner medulla) was fixed in neutral buffered formalin and processed for histology. The volume density (Vv) of cysts in cortex, outer medulla and inner medulla was determined as previously described (Gattone et al., 1995) using point count stereology. These evaluations were performed on cystic and normal mice with and without OPC-31260 treatment. Serum urea nitrogen (SUN) was measured conventionally. Urine osmolarity and structural distortion by cysts-Vv of cysts were evaluated using a three-way analysis of variance.

To determine if activated AVP-$V_2$ receptors played a role in cyst enlargement, cystic mice and their normal littermates were treated on days 3–21 with OPC-31260, a relatively specific AVP-$V_2$ receptor antagonist. Normal mice treated with OPC-31260 excreted hypotonic urine but otherwise appeared healthy. OPC-31260 treatment of cystic mice led to an amelioration of the PKD as evidenced by a reduced cystic enlargement, cyst volume density and azotemia without changes in urine osmolarity.

TABLE 1

| | Aneph. Body Weight (g) | Kid. Weight** as % of TBW | Urine Osmol. | SUN** (mg/dl) | Cyst Vv (%) |
|---|---|---|---|---|---|
| OPC treated-Cystic (11) | 8.0 ± 0.4 | 10.4 ± 0.9* | 362 ± 12** | 28 ± 1.2* | 38 ± 3* |
| Sham treated-Cystic (9) | 7.8 ± 0.3 | 21.1 ± 1.5 | 413 ± 36 | 75 ± 15 | 46 ± 1 |
| OPC treated-Normal (17) | 8.4 ± 0.3* | 1.44 ± 0.02 | 281 ± 9* | 20 ± 1.0* | |
| Sham treated-Normal (7) | 9.7 ± 0.7 | 1.46 ± 0.05 | 420 ± 108 | 16 ± 1.2 | |

\* = $p < 0.05$ treatment effect
\*\* = $p < 0.05$ phenotype difference by ANOVA, (N), Mean ± SEM
TBW = total body weight In conclusion, these data indicate that the development of urinary concentration ability is diminished in murine ARPKD but CD genes associated with this process are overexpressed. Overexpression and activation of AVP–$V_2$ receptor appear to contribute to cystic progression since treatment with a $V_2$ receptor antagonist ameliorates the PKD.

Using the CD1-pcy mouse model of slowly progressive PKD, Applicant examined the efficacy of treatment with the same nonpeptidergic AVP–$V_2$ receptor antagonist (Otsuka Pharmaceutical Co., OPC-31260). The drug was mixed with the ground food of the mice (0.05% for weeks 4–17 weeks of age and 0.1% for weeks 18–20, or 18–24). Sham treated mice received the same ground food but without the drug. The rationale for this treatment is based on the proposed importance of cAMP (the second messenger system used by the AVP–$V_2$ receptor) in the promotion of PKD. Yamaguchi et al. (*J. Am. Soc. Neph.*) have just reported increased urinary cAMP (and renal cAMP) in the pcy mouse model. Normally, a significant amount of urinary cAMP is collecting duct derived from the stimulation of the AVP–$V_2$ receptor. It was hypothesized that using an antagonist for the AVP–$V_2$ receptor would slow the progression of the disease by inhibiting the generation of cAMP. This hypothesis appears to be correct. The progression of pcy PKD can be significantly slowed by treating with a $V_2$ receptor antagonist. This is evidenced by the decreased cyst Vv as shown in Table 1 and decreased kidney weight as a percent of body weight in Tables 1 and 2.

TABLE 2

Treatment of pcy mice from 4 weeks of age to 20 weeks of age (Study 1)

| Group (n) | Body Weight | Kidney Weight as % of TBW* | Sun | Vv Cyst* |
|---|---|---|---|---|
| Cystic Males Control Food (4) | 29.4 ± 0.9 | 4.2 ± 0.3 | 31.2 ± 2.4 | 18.6 ± 0.7 |
| Cystic Males-OPC-31260 Tr. (4) | 28.2 ± 0.6 | 2.8 ± 0.3 | 30.6 ± 1.7 | 11.9 ± 3.1 |

TABLE 2-continued

Treatment of pcy mice from 4 weeks of age to 20 weeks of age (Study 1)

| Group (n) | Body Weight | Kidney Weight as % of TBW* | Sun | Vv Cyst* |
|---|---|---|---|---|
| Cystic Females-Control Food (4) | 28.4 ± 1.8 | 4.2 ± 0.5 | 38.3 ± 2.5 | 20.6 ± 2.5 |
| Cystic Females-OPC-31260 Tr. (4) | 22.9 ± 0.7 | 3.0 ± 0.3 | 28.2 ± 2.6 | 13.5 ± 3.9 |
| Normal Males-Control Food (4) | 35.5 ± 1.0 | 1.30 ± 0.08 | 26.9 ± 2.9 | |
| Normal Males-OPC-31260 Tr. (5) | 34.5 ± 0.3 | 1.34 ± 0.08 | 21.7 ± 1.3 | |
| Normal Female-Control Food (2) | 30.0 ± 0.1 | 1.16 ± 0.01 | 25.9 ± 2.9 | |
| Normal Female-OPC-31260 Tr. (2) | 27.4 ± 2.5 | 1.15 ± 0.03 | 21.1 ± 2.3 | |

\* = $p < 0.05$ for a difference in cystic mice treated with OPC-31260 compared to sham treated mice

TABLE 3

Treatment of pcy mice from 4 weeks of age to 26 weeks of age (Study 2)

| Group (n) | Body Weight | Kidney Weight as % of TBW* |
|---|---|---|
| Cystic Males-Control Food (3) | 26.9 ± 1.3 | 5.7 ± 0.1 |
| Cystic Males-OPC-31260 Tr. (4) | 25.1 ± 0.5 | 4.1 ± 0.3 |
| Cystic Females-Control Food (4) | 22.3 ± 1.4 | 8.5 ± 0.6 |
| Cystic Females-OPC-31260 Tr. (4) | 21.0 ± 0.5 | 4.6 ± 0.4 |
| Normal Males-Control Food (3) | 35.2 ± 1.4 | 1.55 ± 0.04 |
| Normal Males-OPC-31260 Tr. (3) | 35.4 ± 0.6 | 1.43 ± 0.03 |
| Normal Females-Control Food (3) | 28.8 ± 1.4 | 1.28 ± 0.04 |
| Normal Females-OPC-31260 Tr. (3) | 30.3 ± 0.9 | 1.15 ± 0.01 |

\* = $p < 0.01$ for a difference with treatment in cystic mice
\*\* = Mice in this study were just sacrificed so these evaluations are still being performed.

The foregoing beneficial results using $V_2$ antagonist OPC-31260 was unexpected since the clinical circumstances in which a $V_2$ antagonist would be useful generally would be in patients with concentrated urine. Receptor-specific AVP $V_2$ antagonists or "aquaretic agents," able to block the action of AVP in the collecting duct cells and thus to promote water excretion, have been suggested to be of high therapeutic value for the treatment of water retaining disorders such as Syndrome of Inappropriate Anti-Diuretic Hormone secretion (SIADH), liver cirrhosis, certain stages of congestive heart failure and hypertension and nephrotic syndrome. See, e.g., Laszlo, et al., *Pharmacol. Rev.* 43: 73–108 (1991); Mah, et al., *Drugs Future,* 12: 1055–1070 (1987); Manning & Sawyer, *J. Lab. Clin. Med.*, 114: 617–632 (1989); and Sorensen, et al., *J. Int. Med.*, 238: 97–110 (1995). Because PKD is not generally considered a water retaining disease and in fact may manifest nephrogenic diabetes insipidus-like symptoms, $V_2$ receptor antagonists are not intuitively indicated to treat PKD. Indeed, the prior art suggests that treatment with $V_2$ antagonist might exacerbate the existing slightly dehydrated state found in PKD patients. Therefore, the unexpected results found by Applicant suggests the novelty of this treatment. It further suggests the complicated interaction of AVP and the $V_2$ receptor in the regulation of water and solute excretion by the kidney.

Treatment with OPC-31260 in humans with PKD should be administered as an oral dosage pharmacologically sufficient to obtain the desired decrease in renal cAMP levels and cyst size. Based on studies done on the human administration of OPC-31260 (see, e.g., Serradeil-Le Gal, et al., *Characterization of SR121463A, A Highly Potent And Selective, Orally Active Vasopressin 2 Receptor Antagonist,* J. Clin. Invest., 98(12): 2729–38 (Dec. 15, 1996); K. Shimizu, *Aquaretic Effects of the Nonpeptide $V_2$ Antagonist OPC-31260 in Hydropenic Humans,* Kidney International, 48: 220–26 (1995)), an effective oral dose for the treatment of PKD is calculated. OPC-31260 has an effective half-life of about 2–4 hours at the doses described by Serradeil-Le Gal, et al., at FIG. 6. Therefore, a daily oral dose of about 60 mg/kg/day for the chronic treatment of PKD should be sufficient to achieve the desired effects. Any other $V_2$ receptor antagonists can alternatively be used either alone or in conjunction with OPC-31260 to treat human PKD. For example, if SR121463A$^2$ is administered on a equipotent basis, a dose of about 2 mg/kg/day should be employed to treat the disease, although any pharmacologically sufficient dose can be employed. Likewise, Wyeth-Ayerst's VPA-985$^3$ can be administered in an oral dosage of about 2 mg/kg/day or at a dose sufficient to achieve the desired effect of decreasing renal cAMP levels and controlling cyst size. VPA-985 was recently described in Ning, et al., *Forskolin Stimulates cAMP Production By Stimulating Vasopressin $V_2$ Receptors,* J. AM. SOC. NEPH. 8: 23A (September 1997). Alternatively, OPC41061 (Otsuka Pharmaceutical Co.- European Patent No. 450097) can be administered as the $V_2$ receptor antagonist.

$^2$ (1-[4-)N-tert-butylcarbamoyl)-2-methoxybenzene sulfonyl]-5-ethoxy-3 -spiro-[4-(2-morpholinoethoxy)cyclohexane]indol-2-one, fumarate; equatorial isomer).
$^3$ (5-Fluoro-2-methyl-N-[4-(5H-pyrrolo[2,1-c] [1,4] benzodiazepin-10(11H)-yl carbonyl)-3-chlorophenyl]benzamide).

Although several potent peptide vasopressin antagonists are currently available (see Kenter et al., 1988; Manning & Sawyer, 1989; and Laszlow et al., 1991), the therapeutic usefulness of such compounds is limited because of their low oral bioavailability and partial antagonist activity. See Mah & Hofbauer (1988); Brooks et al., (1988); and Albrightson-Winslow et al. (1989). Therefore, none has emerged as a clinically useful anti-diuretic antagonist. This is particularly pertinent to the treatment of PKD because of the chronic nature of the disease. Nevertheless, such peptide $V_2$ antagonists could be administered for short term therapy, if for example, the oral route is unavailable. Peptide $V_2$ antagonists have been described in Huffman & Yim U.S. Pat. No. 4,826,813 and Marshall & Moore U.S. Pat. No. 4,876, 243.

Equivalents

Those skilled in the art will recognize, or be able to ascertain using no more than routine experimentation, many equivalents to the specific embodiments of the invention described herein. Such equivalents are intended to be encompassed by the claims arising out of this application.

I claim:

1. A method for treating polycystic kidney disease in a mammal comprising administering a therapeutically effective amount of a vasopressin $V_2$ receptor antagonist to said mammal.

2. The method of claim 1 wherein said vasopressin $V_2$ receptor antagonist is selected from the group consisting of OPC-31260, OPC-41061, SR121463A, VPA-985 and peptide $V_2$ antagonists.

3. The method of claim 1 wherein said vasopressin $V_2$ receptor antagonist is OPC-31260 administered orally to said mammal in a dose of about 60 mg/kg/day.

4. The method of claim 1 wherein said vasopressin $V_2$ receptor antagonist is SR121463A administered orally to said mammal in a dose of about 2 mg/kg/day.

5. The method of claim 1 wherein said vasopressin $V_2$ receptor antagonist is VPA-985 administered orally to said mammal in a dose of about 2 mg/kg/day.

6. A method for attenuating azotemia and cyst enlargement in polycystic kidney disease in a mammal comprising administering a therapeutically effective amount of a vasopressin $V_2$ receptor antagonist selected from the group consisting of OPC-31260, OPC-41061, SR121463A, VPA-9835 and peptide $V_2$ antagonists.

7. The method of claim 6 wherein said vasopressin $V_2$ receptor antagonist is OPC-31260 administered orally to said mammal in a dose of about 60 mg/kg/day.

8. The method of claim 6 wherein said vasopressin $V_2$ receptor antagonist is SR121463A administered orally to said mammal in a dose of about 2 mg/kg/day.

9. The method of claim 6 wherein said vasopressin $V_2$ receptor antagonist is VPA-985 administered orally to said mammal in a dose of about 2 mg/kg/day.

* * * * *